(12) United States Patent
Wang et al.

(10) Patent No.: US 9,562,916 B2
(45) Date of Patent: Feb. 7, 2017

(54) FULL-AUTOMATIC DETECTING SYSTEM AND METHOD FOR TRANSFORMER

(75) Inventors: Wei Wang, Hangzhou (CN); Jiong Zhu, Hangzhou (CN); Yan Zhang, Hangzhou (CN); Jinjuan Huang, Hangzhou (CN); Jian Wu, Hangzhou (CN); Xiong Li, Hangzhou (CN); Yongjia Zhou, Hangzhou (CN); Huajiang Yan, Hangzhou (CN)

(73) Assignee: Zhejiang Electric Power Corporation, Hangzhou, Zhejiang (CN)

( * ) Notice: Subject to any disclaimer, the term of this patent is extended or adjusted under 35 U.S.C. 154(b) by 869 days.

(21) Appl. No.: 13/980,556

(22) PCT Filed: Nov. 25, 2011

(86) PCT No.: PCT/CN2011/082916
§ 371 (c)(1),
(2), (4) Date: Jul. 18, 2013

(87) PCT Pub. No.: WO2012/163064
PCT Pub. Date: Dec. 6, 2012

(65) Prior Publication Data
US 2013/0297245 A1    Nov. 7, 2013

(30) Foreign Application Priority Data

Jun. 1, 2011  (CN) .......................... 2011 1 0145994
Jul. 14, 2011 (CN) .......................... 2011 1 0197022
(Continued)

(51) Int. Cl.
*G01N 35/00* (2006.01)
*G01R 31/02* (2006.01)
(Continued)

(52) U.S. Cl.
CPC ....... *G01N 35/00584* (2013.01); *G01R 31/027* (2013.01); *H01F 41/00* (2013.01); *G01R 31/01* (2013.01)

(58) Field of Classification Search
USPC ........................................................... 702/82
See application file for complete search history.

(56) References Cited

U.S. PATENT DOCUMENTS

2003/0162344 A1   8/2003  Ishii et al.

FOREIGN PATENT DOCUMENTS

CN      101196414 A     6/2008
CN      201242580 Y     5/2009
(Continued)

OTHER PUBLICATIONS

International Search Report dated Mar. 1, 2012 from corresponding International Application PCT/CN2011/082916.

*Primary Examiner* — Paul D Lee
(74) *Attorney, Agent, or Firm* — Wolf, Greenfield & Sacks, P.C.

(57) ABSTRACT

A full-automatic detecting system and method for a transformer. The system comprises a material delivery line; a feed device; a detection delivery line; insulating test devices; error detecting devices; a laser marking device; a discharge device; and a detection management system. The insulating test devices, the error detecting devices, and the laser marking device are sequentially arranged beside the detection delivery line. The material delivery line, the detection delivery line, and the devices work in coordination, to realize full-automatic detection of the transformer, avoid manual detection errors and improve the sorting accuracy.

16 Claims, 15 Drawing Sheets

(30) Foreign Application Priority Data

| Jul. 14, 2011 | (CN) | .......................... 2011 1 0198519 |
| Jul. 14, 2011 | (CN) | .......................... 2011 1 0198630 |
| Jul. 22, 2011 | (CN) | .......................... 2011 1 0208086 |
| Aug. 24, 2011 | (CN) | .......................... 2011 1 0247680 |

(51) Int. Cl.
    *H01F 41/00*      (2006.01)
    *G01R 31/01*      (2006.01)

(56) References Cited

FOREIGN PATENT DOCUMENTS

| CN | 201285442 Y | 8/2009 |
|---|---|---|
| CN | 201322792 Y | 10/2009 |
| CN | 101592719 A | 12/2009 |
| CN | 201600420 U | 10/2010 |
| CN | 201663045 U | 12/2010 |
| CN | 201740800 U | 2/2011 |
| CN | 201796137 U | 4/2011 |
| CN | 102135607 A | 7/2011 |
| CN | 201965226 U | 9/2011 |
| CN | 202102100 U | 1/2012 |
| CN | 202204923 U | 4/2012 |
| CN | 202204924 | 4/2012 |
| CN | 202210149 | 5/2012 |
| CN | 202305783 U | 7/2012 |
| EP | 1566650 A2 | 8/2005 |
| GB | 740430 | 11/1955 |
| WO | WO 03096037 A1 | 11/2003 |

FULL-AUTOMATIC DETECTING SYSTEM AND METHOD FOR TRANSFORMER

The present application is the national phase of International Application No. PCT/CN2011/082916, entitled "FULL-AUTOMATIC DETECTING SYSTEM AND METHOD FOR TRANSFORMER, filed Nov. 25, 2011, which claims the benefit of priority to the following Chinese patent applications:

Application No. 201110198519.1, entitled "TRANSFORMER AUTOMATION EXAMINING SYSTEM", filed Jul. 14, 2011;

Application No. 201110197022.8, entitled "BUSBAR TYPE CURRENT TRANSFORMER PRIMARY CORE-PENETRATING METHOD", filed Jul. 14, 2011;

Application No. 201110208086.3, entitled "AUTOMATIC WIRE CONNECTING DEVICE FOR PRIMARY END OF MULTI-TURN TYPE TRANSFORMER", filed Jul. 22, 2011;

Application No. 201110247680.3, entitled "SECONDARY WIRE CONNECTING MECHANISM FOR ERROR TESTING", filed Aug. 24, 2011;

Application No. 201110145994.2, entitled "PALLET FOR ON-LINE DETECTING FOR TRANSFORMER", filed Jun. 1, 2011;

Application No. 201110198630.0, entitled "AUTOMATED EXAMINING DEVICE FOR TRANSFORMER", filed Jul. 14, 2011; and all of which applications are hereby incorporated herein by reference to the maximum extent allowable by law.

FIELD OF THE INVENTION

The present application relates to the field of electric power equipment, and in particular to a system and method for examining current transformers.

BACKGROUND OF THE INVENTION

Currently, current transformers used in a power grid proportionally reduce a large current in the primary circuit to a small current required in a secondary measurement circuit, mainly achieving electric isolation between the high voltage end and low voltage end and proportional measurement. The metering current transformer is one of main metering instruments for trade settlement in the power grid, and falls into scope prescribed in the mandatory test specifications of China. Each metering current transformer can only be put into normal use after being verified to be qualified by passing the initial examination and the periodic examinations. With rapid development of economy, both the increment and the holding of the metering current transformers have grown sharply. The traditional manual examining method, due to problems such as low working efficiency, labor-intensive and intervening to examining results by manual wire connecting, can not fulfill the increasing demand for examining transformers any more, thus it is necessary to develop a system for examining current transformers full-automatically.

In a conventional device for examining transformers, a semi-automatic working mode is adopted, wire connecting and disconnecting are performed manually, and the examining device performs the basic error examinations automatically. However, insulation tests, such as the insulation resistance test, the withstand voltage test, the inter-turn insulation test and the magnetic saturation margin test, are all required to be performed manually, so the working efficiency is rather low, and some examinations even can not be performed owing to the limitation of the capacity of the examining devices.

Low-voltage current transformers are divided into two types: bus-type (bus mode) current transformers and multi-turn-type (multi-turn mode) current transformers. The primary winding connecting methods for the two types of current transformers are different and external dimensions, diameters and positions of center-holes for bus-type current transformers of different transformation ratios are different, thus the system for examining current transformers needs to meet the requirement of different wire connecting modes and different dimensions from bus-type current transformers and multi-turn-type current transformers. A single conventional device for examining current transformers full-automatically can not fulfill the demand for examining huge numbers of transformers, and do not have the advantages of automatic production line, hence integration of multiple devices for examining current transformers is required in the system for examining transformers.

To sum up, it is significant to develop a system for examining current transformers full-automatically, which is adapted for bus-type current transformers and multi-turn-type current transformers, and is an integration of multiple examining devices and a conveying line.

SUMMARY OF THE INVENTION

The technical problems to be solved and the technical tasks set force in the present application are to improve the technical solutions in the prior art and propose a system for examining current transformers full-automatically, so as to achieve full-automatic examination and improve the efficiency and accuracy of the examination.

Therefore, the present application adopts technical solutions as follows.

A system for examining transformers full-automatically according to embodiments of the present application, includes: a material conveying line for conveying turnover boxes so as to deliver turnover boxes loaded with transformers to be examined from a storage system to a material charging station and deliver turnover boxes loaded with transformers having been examined located at a material discharging station back to the storage system; a material charging device located beside the material charging station of the material conveying line, for moving transformers located at the material charging station on the material conveying line to the examination conveying line; an examination conveying line for moving transformers to each examining device; an insulation test device (preventive test device) for insulation resistances detecting, power frequency withstand voltages testing and inter-turn insulations testing of transformers; an error examining device for detecting basic errors and magnetic saturation margins of transformers; a Laser marking device for imprinting identification information on qualified transformers; a material discharging device located beside the material discharging station on the material conveying line for transferring transformers having been examined from the examination conveying line to the material conveying line, an examination management system for controlling coordinate operation of respective devices, the material conveying line and the examination conveying line and sorting transformers accurately according to feedback information from insulation test device and error examining device; the insulation test device, the error examining device and the Laser marking device are sequentially arranged beside the examination conveying line. The material conveying line, the examination conveying line and each device operate coordinately so as to examine the transformers full-automatically with high efficiency, avoid fault of the manual examination, and improve accuracy of sorting. Replacing the traditional method of pasting certificate of quality with laser marking facilitates management and usage of transformers.

As a further improvement and supplement of the above technical solutions, the present application further includes additional technical features as follows.

The system for examining transformers full-automatically according to embodiments of the present application further includes: an appearance inspection device located ahead of the insulation test device and adapted to take photos of the appearance of each transformer and checking; multiple testing device sets arranged side by side in the system with each of the testing device set being composed of one insulation test device and one error examining device which are sequentially arranged on the frame body beside the examination conveying line; the head end and tail end of the examination conveying line are connected, the examination conveying line is provided with pallets for bearing transformers which match the examination conveying line so as to convey transformers to an appearance inspection station, an insulation test station, an error examining station and a laser marking station in sequence, thus conveying transformers for full on-line examination. Multiple testing device sets operate coordinately at the same pace and thus the efficiency is improved. The appearance inspection device includes a camera, a photo storage unit, and a photo process unit. The camera takes photos for the transformers one by one at the appearance inspection station, and stores by naming the photos according to certain rules, and through image recognition and content comparison, it is analyzed whether the name plates of transformers being examined have full and correct contents and the bodies of transformers are in good condition.

The material conveying line includes a frame body, a driving motor arranged on the frame body for driving a belt to move forward, a belt connected with a rotating shaft of the driving motor, and/or a stop mechanism arranged on the frame body for stopping transformers on the belt accurately, and/or a counter arranged on the frame body for counting transformers, and/or a bar code scanner arranged on the frame body for entering information of transformers and a sorting mechanism for sorting transformers; the input end and output end of the material conveying line are adapted to connect an entrance and an exit of the storage system respectively. The material conveying line may convey transformers and electricity meters of multiple mixed types and may sort transformers and electricity meters of multiple types accurately, and may feed materials of fixed quantity and fixed type to the corresponding system for examining transformers automatically, and allowing transformers to be examined to be positioned accurately at material charging/discharging stations, so as to wait for operation of the material charging and discharging devices.

The material charging device includes a material charging robot for placing the transformers to be examined from the material conveying line to the pallets on the examination conveying line precisely. The material charging robot is provided with a material charging manipulator, a controller for controlling the operation of the manipulator, and a material charging fixture connected with the lower end of the manipulator, a transit platform for positioning transformers precisely. The material discharging device includes a material discharging robot for placing transformers having been examined from the pallets on the examination conveying line to the material conveying line. The material discharging robot is provided with a material discharging manipulator, a controller for controlling the operation of the manipulator, and a material discharging fixture capable of being connected with the lower end of the material discharging manipulator. The material charging/discharging fixture may be applicable for transformers of all types.

The material charging robot is provided with a positioning platform for positioning transformers precisely, transformers are grasped from the material conveying line and are placed on the positioning platform of the material charging robot by the material charging manipulator for being positioned. After transformers are precisely re-positioned according to different specifications thereof on the positioning platform, the transformers will be grasped again and placed onto the pallets located on the examination conveying line by the material charging manipulator.

Each of the insulation test device and the error examining device includes a second examining unit and a first examining unit which are sequentially arranged on the frame body beside the conveying line along the direction of advance of the examination conveying line. The connections between the power source and the primary large current conductors of the first examining unit and the second examining unit are switched by means of a relay. After automatic examining devices are applied, the paces of examining transformers speed up, the shortage of time for heat dissipating due to the long time and continuous large current testing will cause temperature rising too high and even may damage examining devices. Each of the examining devices is divided into two examining units which are electrified at different time, and at one time only one set of transformers and one examining unit are allowed through large current, the other set of transformers and the other examining unit are on standby, and the examining unit may dissipate heat in this period of time. Controlling the temperature rising in the whole process of examining, can meet the requirement of full automatic and continuous large current testing.

Each of the first examining unit and the second examining unit includes a primary wire connecting mechanism for bus-type current transformers, a primary wire connecting mechanism for multi-turn-type current transformers and a secondary wire connecting mechanism. The primary wire connecting mechanism for bus-type current transformers and the primary wire connecting mechanism for multi-turn-type current transformers are capable of moving backwards and forwards, and are respectively arranged on both sides of conveying line respectively when both of the primary wire connecting mechanisms are on standby. The primary wire connecting mechanism for bus-type current transformers and the primary wire connecting mechanism for multi-turn-type current transformers are applicable to examine bus-type transformers and multi-turn type transformers respectively. The arrangement of one being arranged on one side and the other being arranged on the other side of examination conveying line when on standby may avoid interference between each other. When one transformer is being examined, the corresponding primary wire connecting mechanism will move towards the examining conveying line.

The primary wire connecting mechanism for bus-type current transformers includes a bus-type back and forth driving assembly capable of moving backwards and forwards on the frame body, an inlet side manipulator and an output side manipulator being connected with the left and right ends of the back and forth driving assembly respectively and capable of moving upwards and downwards, pneumatic claws arranged at lower ends of the inlet side manipulator and the output side manipulator and can open and shut, a core-penetrating copper bar gripped by the pneumatic claws and adapted to penetrate multiple bus-type current transformers; wherein the outer sides of the pneumatic claws are provided with column-shaped copper heads for connecting the large current conductor, the two pneumatic claws and the core-penetrating copper bar of the primary wire connecting mechanism for bus-type current transformers can form a closed circuit so as to examine multiple bus-type current transformers with primary sides in series connection.

The primary wire connecting mechanism for multi-turn-type current transformers includes a back and forth driving assembly capable of moving backwards and forwards on the frame body, multiple connecting assemblies arranged side by side on the back and forth driving assembly for connecting in series the primary sides of the corresponding multi-turn-type current transformers. The connecting assembly includes upper and lower conductive holding members capable of holding the terminals on the primary sides of the multi-turn-type current transformers.

The secondary wire connecting mechanism includes an up and down driving assembly for secondary wire connecting which is connected with the frame body and capable of moving upwards and downwards, the lower end of the up and down driving assembly for secondary wire connecting is provided with multiple vertical conductive bars for connecting the secondary ends of current transformers.

The examination management system is provided with a task management functional module, adapted to obtain a working task from a production scheduling platform, apply with the storage system for sending materials out, and decompose the task for different examining units and stations according to the production task; a conveyance control functional module, adapted to trigger robots to charge and discharge materials automatically, control the conveying line to distribute the current transformers to be examined to corresponding examining stations, and charge and discharge materials in sequence for a plurality sets of examining devices and multiple examining units; a examining control functional module, adapted to automatically perform the connecting of the primary winding and the secondary winding required for the examinations of current transformers, control the current booster and voltage booster and measure to perform the examinations, and store error data; a data process and analysis functional module, adapted to determine whether a current transformer is examined to be qualified, and make analysis and statistics for the finishing rate and failure rate of the examining tasks for current transformers.

The present invention further provided a method for examining transformers full-automatically, including the steps as follows:

1) material feeding step, where transformers to be examined are conveyed from an exit of the storage system to the material charging station by material conveying line;

2) material charging step, where transformers on the material conveying line are grasped and placed onto the pallets located on the examination conveying line by a material charging robot, the pallets are bound with bar code information of transformers, and information of transformers is recorded;

3) appearance inspection step, where the pallets are brought along by the examination conveying line and enter into the appearance inspection station, a camera takes photos of the transformers, and through contrasting the photos taken to the corresponding photos stored, the appearance inspection device analyzes whether the content of a name plate of a transformer to be examined is complete and a body of the transformer to be examined is in good condition, and records;

4) insulation test step, where the pallets arrive at insulation test stations along with the examination conveying line, certain numbers of pallets are brought along by the examination conveying line and enter into the corresponding insulation test stations, the insulation test device at the insulation test stations connects primary windings and secondary windings of transformers, programmed control power source outputs voltages of 380V or 220V to a current booster and a voltage booster, so that the current booster generates a low voltage large current, the voltage booster generates DC and AC voltages according to different testing items to perform the inter-turn insulation test, the insulation resistance test and the power frequency withstand voltage test in sequence for low voltage current transformers;

5) error examining step, where when the insulation test finishes, the transformers being examined flow into the error examining stations along with the examination conveying line, the error examining device on the error examining stations connects the primary windings and the secondary windings of transformers, the programmed control power source outputs voltages of 380V or 220V to the current booster, the current booster generates a low voltage large current which flows through primary windings of transformers to be measured in series connection via primary leads connected to the output end of the current booster, the output currents of the secondary windings of transformers are measured by a check gauge for transformers connected to the secondary winding connecting mechanism, the error test and the magnetic saturation margin test are performed, full-automatic examination is realized, and unqualified products are recorded;

6) laser marking step, after the error examining finishes, the pallets enter into the laser marking station along with the examination conveying line, the laser marking machine will etch a section of codes on the body of the transformer examined to be qualified for indicating the information of being examined to be qualified, an examination date, and the personnel performing the examination; the transformers examined to be unqualified flow into the material discharging station automatically and wait for abnormal handling without being marked by laser; and 7) material discharging step, the qualified transformers on the pallets on the examination conveying line are grasped and placed in the boxes located on the material conveying line by a material discharging robot, and after the transformers are boxed, the boxes are conveyed to the storage system along with the material conveying line.

Each of the insulation test device and the error examining device is divided into a first examining unit and a second examining unit. A batch of twelve transformers is divided into two equal groups which enter into the first examining unit and the second examining unit in sequence. When the first examining unit of the insulation test device electrifies and tests six transformers, the second examining unit of the insulation test unit finishes wires connecting of the first windings and the second windings, and waits for electrifying and testing. After the first examining unit of the insulation test device finishes electrifying and testing the six transformers, the second examining unit of the insulation test device begins the electrifying and testing. Subsequently, six transformers located at the first examining unit of the insulation test device flow into the first examining unit the error examining device, and are electrified and tested after wires being connected. After the second examining unit of the insulation test device finishes electrifying and testing six transformers, the six transformers having flowed into the second examining unit of the error examining device are electrified and tested.

Benefit effect: the full-automatic examining system for examining transformers according to embodiments of present application with wide scope of application may be adapted to examine bus-type current transformers as well as multi-turn-type current transformers. Multiple sets of examining devices operate coordinately, and robots perform material charging and discharging automatically, so that transformers are examined full-automatically with high efficiency. Traditional method of pasting certificate of quality is replaced with laser marking, thus facilitating the subsequent management. Power is by two units alternatively so that the temperature rising of the devices is controlled, thus facilitating the improvement of service life of the devices and stability and accuracy of the examination.

Figure 1:
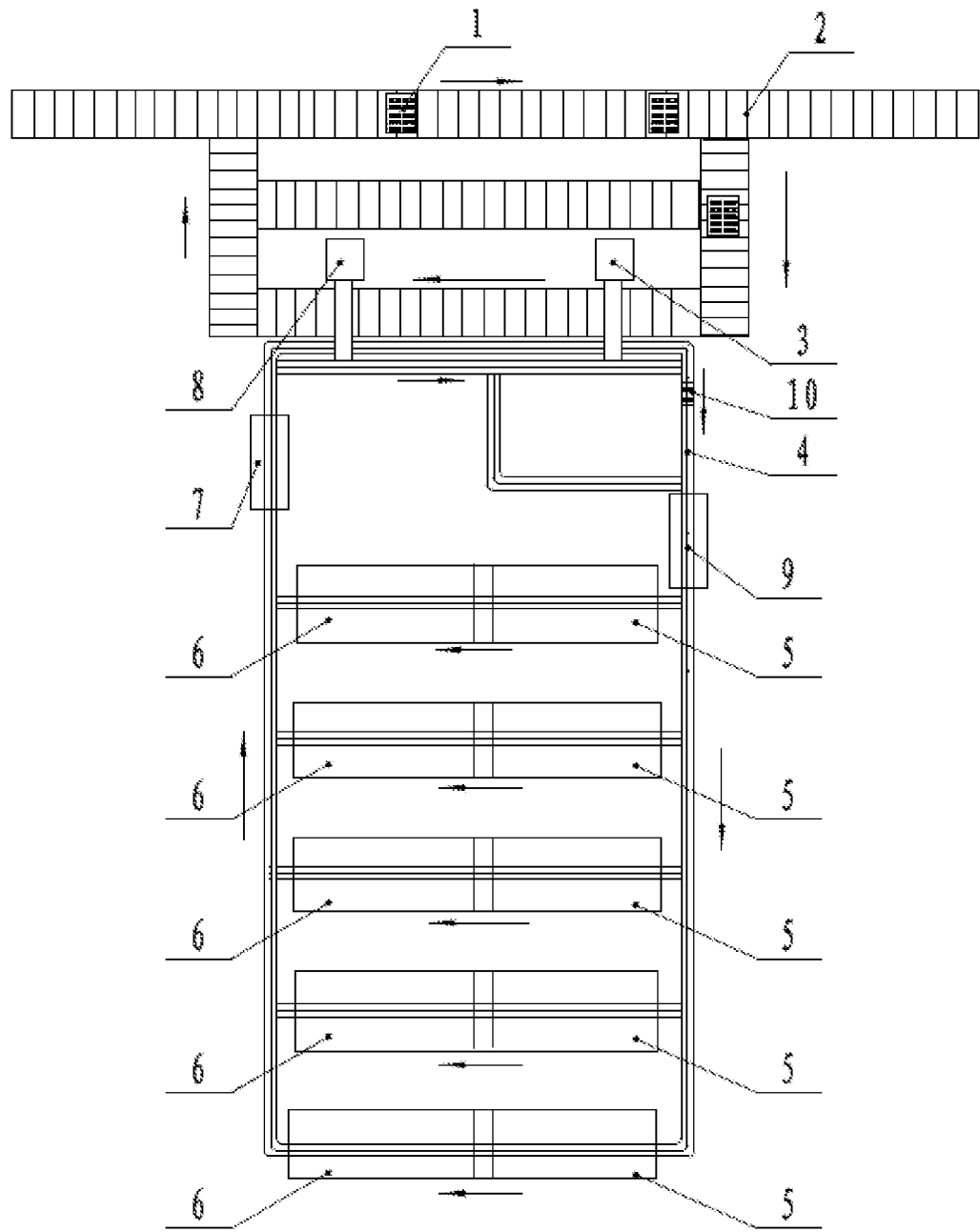
FIG. 1 is a schematic structural view of the system for examining transformers full-automatically according to embodiments of the present application.

| Reference numerals in FIGS. 1 to 16 | |
| --- | --- |
| 1: turnover box; | 2: material conveying line; |
| 3: material charging device; | 4: examination conveying line; |
| 5: insulation test device; | 6: error examining device; |
| 7: laser marking device; | 8: material discharging device; |
| 9: appearance inspection device; | 10: pallet. |

DETAILED DESCRIPTION OF THE INVENTION

The technical solutions of the present application will be described below in detail in conjunction with the accompanying drawings of the specification.

Referring to FIG. 1, which is a schematic structural view of the system for examining transformers full-automatically according to embodiments of the present application.

The system for examining transformers full-automatically according to embodiments of the present application includes: a material conveying line 2, a material charging device 3, an examination conveying line 4, an appearance inspection device 9, insulation test devices 5, error examining devices 6, a laser marking device 7, a material discharging device 8, and an examination management system.

The material conveying line 2, for conveying turnover boxes 1, delivers turnover boxes 1 charged with transformers to be examined from a storage system to a material charging station and delivers the turnover boxes 1 charged with transformers having been examined located at a material discharging station back to the storage system.

The material charging device 3, located beside the material charging station of the material conveying line 2, is adapted to move transformers located at the material charging station on the material conveying line 2 to the examination conveying line 4.

The examination conveying line 4, is adapted to move transformers to stations corresponding to respective devices.

The appearance inspection device 9, is adapted to take photos for the appearance of each transformer and process the photos.

The insulation test devices 5, are adapted to detect insulation resistances, test power frequency withstand voltages and test inter-turn insulations of transformers.

The error examining devices 6, are adapted to detect basic error measurements and magnetic saturation margins of transformers.

The laser marking device 7, is adapted to imprint identification information on qualified transformers.

The material discharging device 8, located beside the material discharging station on the material conveying line 2, is adapted to transfer transformers having been examined from the examination conveying line 4 to the material conveying line 2, and to sort the transformers qualified and unqualified into different turnover boxes 1.

Examination management system, is adapted to control coordinate operation of respective devices, the material conveying line 2 and the examination conveying line 4, and to made determination on the examination result of transformers according to feedback information from the insulation test devices 5 and the error examining devices 6.

The appearance inspection device 9, the insulation test devices 5, the error examining devices 6 and the laser marking device 7 are sequentially arranged along the direction of advance of the examination conveying line 4.

The system for examining transformers full-automatically according to embodiments of the present application may be provided with multiple testing device sets arranged side by side. Specifically, the system for examining transformers full-automatically according to embodiments of the present application may be provided with two or over two testing device sets. FIG. 1 shows a case in which five testing device sets are provided.

Each testing device set includes one insulation test device 5 and one error examining device 6.

The head end and tail end of the examination conveying line 4 are connected, the examination conveying line 4 is provided with pallets 10 matching the examination conveying line 4 which are adapted to load transformers.

The material conveying line 2 includes a frame body, a driving motor arranged on the frame body for driving a belt to move forward, a belt connected with the rotating shaft of the driving motor, and/or a stop mechanism arranged on the frame body for stopping transformers on the belt accurately, and/or a counter arranged on the frame body for counting transformers, and/or a bar code scanner arranged on the frame body for entering information of transformers and a sorting mechanism for sorting transformers.

The input end and output end of the material conveying line 2 are adapted to connect the entrance and exit of the storage system respectively.

The material charging device 3 includes a material charging robot for placing transformers to be examined from the material conveying line 2 to the pallets 10 on the examination conveying line 4 precisely.

The material charging robot includes a material charging manipulator, a controller for controlling the operation of the material charging manipulator, a material charging fixture connected with the lower end of the manipulator, and a transit platform for re-positioning transformers.

The material discharging device 8 includes a material discharging robot for placing transformers having been examined from the pallets 10 on the examination conveying line 4 to the material conveying line 2.

The material discharging robot includes a material discharging manipulator, a controller for controlling the operation of the material discharging manipulator, and a material discharging fixture connected with the lower end of the material discharging manipulator.

The material charging robot is provided with a positioning platform for positioning transformers precisely. Instrument transformers are grasped from the material conveying line 2 and are placed on the positioning platform of the material charging robot by the material charging manipulator for being positioned. After transformers are precisely re-positioned on the positioning platform according to different specifications of the transformers, the transformers will be grasped again and placed onto the pallets 10 located on the examination conveying line 4 by the material charging manipulator.

Each of the insulation test devices 5 and the error examining devices 6 includes a second examining unit and a first examining unit which are sequentially arranged on the frame body beside the conveying line 4 along the direction of advance of the examination conveying line 4.

The connections between the power source and the large primary current conductor of the first examining unit and the second examining unit are switched by means of a relay.

Each of the first examining unit and the second examining unit includes a primary wire connecting mechanism for bus-type current transformers, a primary wire connecting mechanism for multi-turn-type current transformers and a secondary wire-connecting mechanism.

The primary wire connecting mechanism for bus-type current transformers and the primary wire connecting mechanism for multi-turn-type current transformers are capable of moving backwards and forwards, and are respectively arranged on both sides of the examination conveying line (4) respectively when on standby.

The primary wire connecting mechanism for bus-type current transformers includes a bus-type back and forth driving assembly, an inlet side manipulator and an output side manipulator, pneumatic claws, and a core-penetrating copper bar.

The bus-type back and forth driving assembly, is capable of moving backwards and forwards on the frame body.

The inlet side manipulator and the output side manipulator are connected with the left and right ends of the back and forth driving assembly respectively and are capable of moving upwards and downwards.

The pneumatic claws, are arranged at lower ends of the inlet side manipulator and the output side manipulator and can open and shut.

The core-penetrating copper bar, gripped by the pneumatic claws, is adapted to penetrate multiple bus-type current transformers.

The outer sides of the pneumatic claws are provided with column-shaped copper heads for connecting the large current conductor, the two pneumatic claws and the core-penetrating copper bar of the primary wire connecting mechanism for bus-type transformers can form a closed circuit so as to examine multiple bus-type current transformers with primary sides of the transformers being in series connection.

The primary wire connecting mechanism for multi-turn-type current transformers includes a back and forth driving assembly capable of moving backwards and forwards on the frame body, multiple connecting assemblies arranged side by side on the back and forth driving assembly for connecting in series primary sides of the corresponding multi-turn-type current transformers.

The connecting assembly includes upper and lower conductive holding members capable of holding terminals on the primary side of multi-turn-type current transformers.

The secondary wire connecting mechanism includes an up and down driving assembly for secondary wire connecting which is connected with the frame body and capable of moving upwards and downwards, the lower end of the up and down driving assembly for secondary wire connecting is provided with multiple vertical conductive bars for connecting to the secondary end of transformers.

The insulation test device 5 has two types of mechanisms for connecting the primary winding which are adapted for bus-type transformers and multi-turn-type transformers respectively.

The primary connecting mechanism for multi-turn-type transformers (i.e. multi-turn-type current transformers) is in a clamp-shaped structure. Two sets of clamp-shaped fixtures are provided for each multi-turn-type transformer so as to clamp primary bus bars on both sides of each transformer respectively, at this point, the primary lead, the clamp-shaped fixtures and the primary winding of the transformer form a closed circuit with large current. When on standby, the clamp-shaped fixtures rest on one side of the examination conveying line, and when multi-turn-type transformers are conveyed to the examining station, the clamp-shaped fixtures translate laterally and approach the examination conveying line 4 to perform the primary connecting operation.

Figure 15:
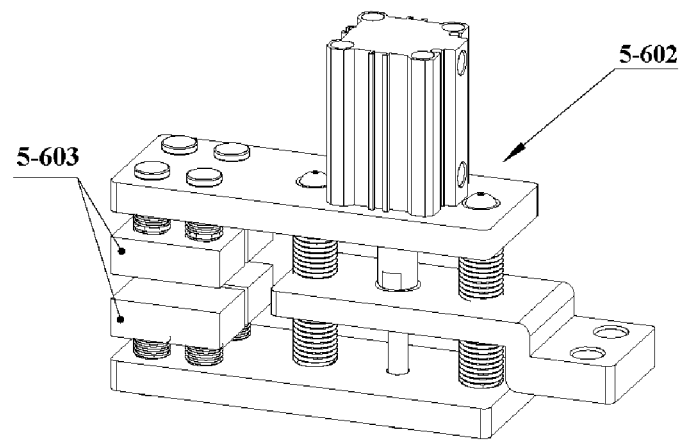
FIG. 15 is a schematic structural view of a primary wire connecting mechanism for multi-turn-type current transformers according to embodiments of the present application.

As shown in FIG. 15, the primary wire connecting mechanism for multi-turn-type current transformers includes a back and forth driving assembly for multi-turn-type current transformers which is capable of moving backwards and forwards on the frame body. Multiple connecting assemblies 5-602 arranged side by side on the back and forth driving assembly for multi-turn-type current transformers are adapted to connect primary sides of the corresponding multi-turn-type current transformers in series. The connecting assembly 5-602 includes upper and lower conductive holding members 5-603 capable of holding terminals on the primary side of multi-turn-type current transformers.

Figure 6:
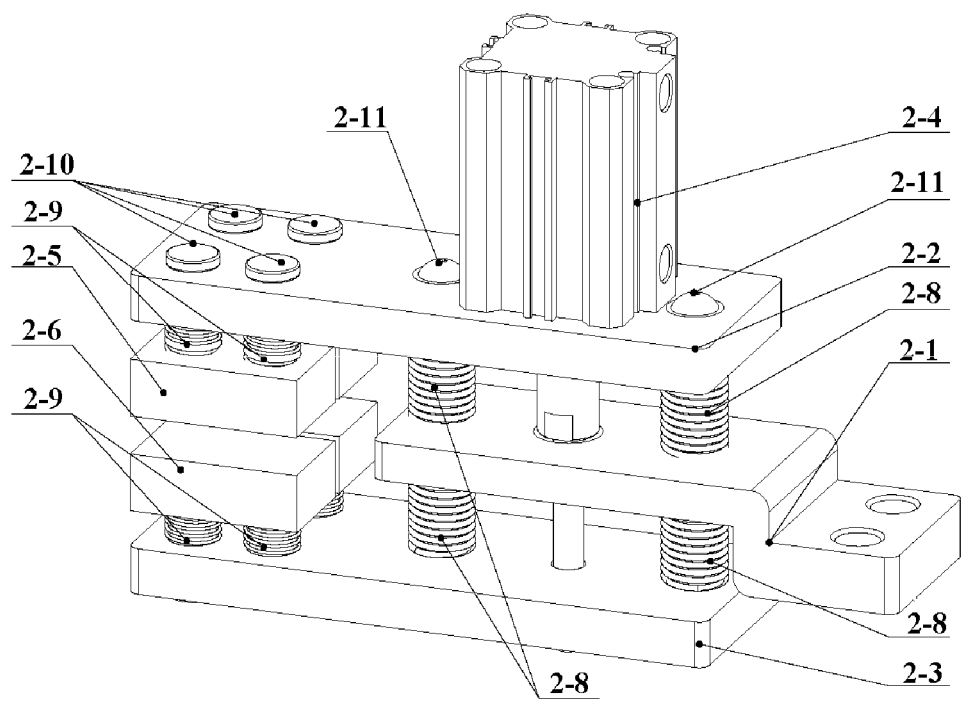
FIG. 6 is a schematic perspective view of a primary connecting mechanism for multi-turn-type current transformers according to embodiments of the present application.
Figure 7:
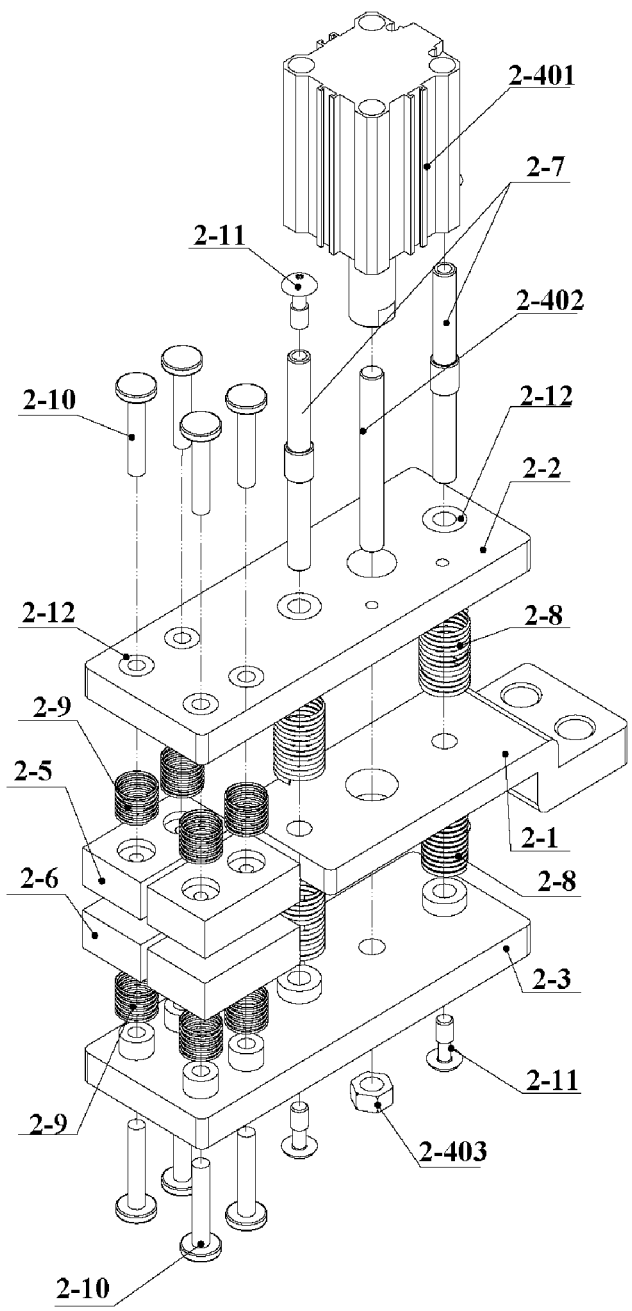
FIG. 7 is an exploded view of the primary connecting mechanism for multi-turn-type current transformers according to embodiments of the present application.

The primary connecting mechanism for multi-turn-type current transformers is as shown in FIGS. 6 and 7.

The primary connecting mechanism for multi-turn-type current transformers may include a "Z"-shaped connecting bracket 2-1, an upper insulation plate 2-2 arranged above the connecting bracket 2-1, a lower insulation plate 2-3 arranged below the connecting bracket 2-1, a cylinder 2-4 connected to the lower insulation plate 2-3 with a cylinder body 2-401 fixed on the upper insulation plate 2-2 and a movable rod 2-402 passing through the connecting bracket 2-1, an upper conductive holding member 2-5 and a lower conductive holding member 2-6 which are located between the upper insulation plate 2-2 and the lower insulation plate 2-3 and are adapted to hold the primary terminal of multi-turn-type current transformers, multiple bracket guiding rods 2-7 for guiding which are arranged by passing the connecting bracket 2-1 with upper and lower ends of each of the guiding rods 2-7 slidably connected with the upper and lower insulation plates 2-2, 2-3 respectively. The lower end of the movable rod 2-402 is in threading connection with a nut 2-403 with the top surface of the nut 2-403 abutting against the bottom surface of the lower insulation plate 2-3, the multiple bracket guiding rods 2-7 are parallel to the movable rod of the cylinder 2-4 and are arranged respectively on both sides of the movable rod 2-402 of the cylinder 2-4, and small compression springs 2-8 are sleeved on portions of the bracket guiding rods 2-7 that between the upper insulation plate 2-2 and the connecting bracket 2-1 as well as between the lower insulation plate 2-3 and the connecting bracket 2-1.

The upper conductive holding member 2-5 may be slidably connected to the corresponding upper insulation plate 2-2 by means of holding-member guiding rods 2-10 with big compression springs 2-9 sleeved on the guiding rods 2-10. The lower conductive holding member 2-6 may be slidably connected to the corresponding lower insulation plate 2-3 by means of holding-member guiding rods 2-10 with big compression springs 2-9 sleeved on the guiding rods 2-10. Large current conductors usable for examining and testing transformers are fixed on the top portion of each of the holding-member guiding rods 2-10.

Guiding rod holes on the upper and lower insulation plates 2-2, 2-3 through which the bracket guiding rods 2-7 and the holding-member guiding rods 2-10 pass are provided with sliding bearings 2-12 therein, the sliding bearings 2-12 protrude from the inner surfaces of the upper and lower insulation plates 2-2, 2-3 with the big and small compression springs 2-9, 2-8 being sleeved on the sliding bearings 2-12.

The upper and lower ends of the bracket guiding rods 2-7 threadingly connect to the cover plate bolts 2-11, with the cover plate bolts 2-11 being capable of abutting against the upper and lower insulation plates 2-2 and 2-3.

The upper and lower conductive holding members 2-5, 2-6 are located at front of the connecting bracket 2-1. Each of the upper and lower conductive holding members 2-5, 2-6 is provided with two holding-member guiding rods 2-10. The connecting bracket 2-1 is provided with four or two bracket guiding rods 2-7, with the movable rod of the cylinder 2-4 being located at the middle of the bracket guiding rods 2-7.

The upper insulation plate 2-2 is connected with two upper conductive holding members 2-5 arranged right and left, with the lower insulation plate 2-3 being connected with two lower conductive holding members 2-6 opposite to the upper conductive holding members 2-5. Rear end of connecting bracket 2-1 is fixedly connected with the big splint movable backwards and forwards. Multiple connecting brackets 2-1 are fixed on one big splint so as to drag multiple wire connecting devices simultaneously. The upper and lower insulation plates 2-2, 2-3 of the wire connecting devices on the leftmost or rightmost side of the big splint are respectively provided with an upper conductive holding member 2-5 and a lower conductive holding member 2-6 opposite to the upper conductive holding member 2-5.

When in operation, the movable rod of the cylinder 2-4 contracts, driving the upper and lower insulation plates 2-2, 2-3 move relative to each other, so that the upper and lower holding members 2-5, 2-6 connected with the upper and lower insulation plates 2-2, 2-3 follow to move relative to each other so as to clamp the primary bus bars of multi-turn-type transformers, thus connecting wires automatically.

Figure 14:
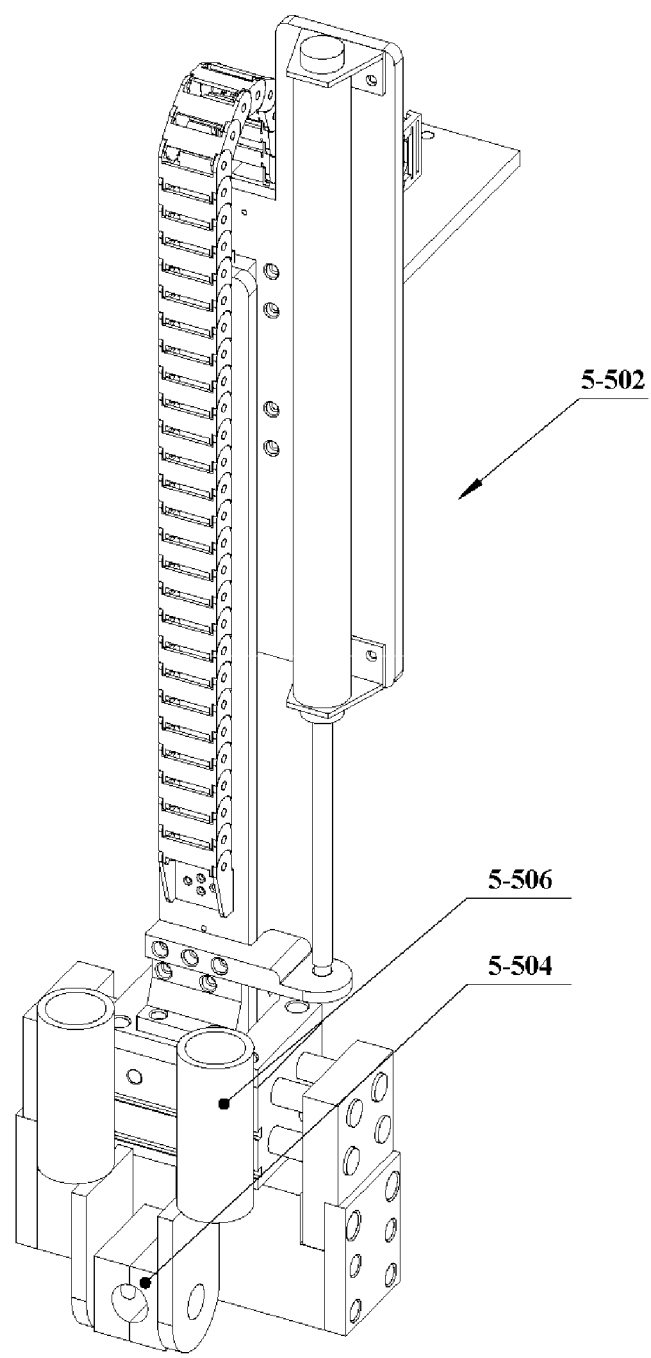
FIG. 14 is a schematic structural view of the primary wire connecting mechanism for bus-type current transformers according to embodiments of the present application.

As shown in FIG. 14, the primary wire connecting mechanism for bus-type current transformers includes a back and forth driving assembly for bus-type current transformers which is movable backwards and forwards on the frame body, an inlet side manipulator 5-502 and output side manipulator which are movable upwards and downwards and connected with right and left ends of the back and forth driving assembly respectively, pneumatic claws 5-504 arranged at lower ends of the inlet side manipulator 5-502 and the output side manipulator and capable of opening and shutting, a core-penetrating copper bar matching with the two pneumatic claws 5-504 for penetrating multiple bus-type current transformers. The outer sides of the pneumatic claws 5-504 are provided with column-shaped copper heads 5-506 for connecting large current conductors. The two pneumatic claws 5-504 together with the core-penetrating copper bar of the primary wire connecting mechanism for bus-type current transformers can form a closed circuit so as to examine multiple bus-type current transformers with the primary sides of the transformers being in series connection.

The primary connecting mechanism for bus-type current transformers (i.e. bus-type current transformers 1-3) is in a core-penetrating copper bar structure (FIGS. 3 and 5 may be referred in detail), the core-penetrating copper bar 1-2 is gripped by manipulators on both sides of the core-penetrating copper bar 1-2 respectively. In the process of connecting the primary side, the core-penetrating copper bar 1-2 and the manipulators should be located right above the conveying line 1-4 (i.e. the examination conveying line 4 in FIG. 1). The inlet side manipulator 1-5 for bus-type current transformers 1-3 releases the copper bar and moves upwards, the output side manipulator 1-6 solely grips the copper bar, bus-type current transformers 1-3 to be examined flow into the insulation test device 5 along with the examination conveying line 4 and are penetrated in sequence by the core-penetrating copper bar 1-2 and will be positioned accurately at a fixed examining station by the stop mechanism in the conveying line. After a group of bus-type current transformers 1-3 are penetrated entirely by the core-penetrating copper bar 1-2, the input side manipulator 1-5 moves downwards and grips the core-penetrating copper bar 1-2, at this point, the primary lead, the conductive part of the manipulator and the core-penetrating copper bar 1-2 form a closed circuit with large current. When the test finishes, the output side manipulator releases the copper bar and moves upwards, the stop mechanism of the conveying line stretches out, and bus-type current transformers 1-3 flow out of the core-penetrating copper bar 1-2 along with the pallets 10 and flow into the subsequent error examining devices.

For facilitating the understanding by the person skilled in the art, the method of primary core-penetrating for bus-type current transformers is explained as follows:

Conveying line 1-4 (i.e. the examination conveying line 4 in FIG. 1) conveys bus-type current transformers 1-3 in rows, before bus-type current transformers 1-3 enter examining stations, the inlet side manipulator 1-5 raises up, the output side manipulator solely grips one side of the core-penetrating copper bar 1-2 with the other side of the core-penetrating copper bar being in suspension, rows of bus-type current transformers 1-3 are penetrated by the core-penetrating copper bar 1-2 along with the forward moving of the examination conveying line 4. The conveying line 1-4 stops moving, and the inlet side manipulator 1-5 comes down to grip the core-penetrating copper bar 1-2, till the examination of bus-type current transformers 1-3 finishes, the output side manipulator 1-6 releases the core-penetrating copper bar 1-2 and raises up, the inlet side manipulator 1-5 grips one side of the core-penetrating copper bar 1-2 with the other side of the core-penetrating copper bar being in suspension, the conveying line 1-4 is started so as to bring bus-type current transformers 1-3 to keep on moving forwards and leave the examining station, the output side manipulator 1-6 comes down to grip the core-penetrating copper bar 1-2, and till then the primary core-penetrating for bus-type current transformers is done.

Each of the lower ends of the output side manipulator 1-6 and the inlet side manipulator 1-5 is provided with a gripping part which is provided with a holding hole 1-511 for holding the core-penetrating copper bar 1-2.

The holding hole 1-511 is arranged to be tilted upwards so that the core-penetrating copper bar 1-2 is held to be tilted for counteracting the downward movement of the suspending end of the core-penetrating copper bar 1-2 when the core-penetrating copper bar 1-2 is held with one side in suspending. The tilting angle of the holding hole may be from 0.05° to 2°.

For improving the accuracy of the core-penetrating, bus-type current transformers 1-3 are placed onto the pallets 1-7 (i.e. the pallet 10 in FIG. 1), and are placed on the conveying line 4 after having been positioned by the pallets 1-7. The lower end surface of the pallets 1-7 contact the conveying line 1-4, and the lower end surface of the pallets 1-7 is provided with two guiding pins. The conveying line 4 is provided with a stop mechanism matching with the guiding pins so as to accurately position the pallet 1-7 at the examining station. After core-penetrating, the core-penetrating copper bar 1-2 is in clearance fit with bus-type current transformers 1-3 in which the clearance may be from 0.5 mm to 2 mm.

For allowing the conveying line 1-4 to be applicable to other types of transformers, a back and forth driving device is additionally provided. The inlet side manipulator 1-5 and the output side manipulator 1-6 are respectively arranged on the right and left sides of a back and forth driving device, and the back and forth driving device brings the inlet side manipulator 1-5 and the output side manipulator 1-6 to move backwards and forwards synchronously. When transformers to be examined are bus-type current transformers 1-3, the back and forth driving device moves so that the inlet side manipulator 1-5 and the output side manipulator 1-6 are located right above the conveying line 1-4. When transformers to be examined are multi-turn-type current transformers, the back and forth driving device and the manipulators are located at the same side of the conveying line 1-4 and on standby.

The back and forth driving device includes back and forth driving cylinders 1-501 arranged on the frame body 1-1 laterally, top plates 1-502 each fixedly connected to the movable end of a respective one of the back and forth driving cylinders 1-501 and slidably and laterally connected with the frame body 1-1. Operation of the back and forth driving cylinders 1-501 brings the top plates 1-502 to slide backwards and forwards on the frame body 1-1. The back and forth driving device is provided with two top plates 1-502 fixedly connected with the output side manipulator 1-6 and the inlet side manipulator 1-5 respectively. The two top plates 1-502 are fixedly connected with each other by means of a connecting rod 1-512. Each of the output side manipulator 1-6 and the inlet side manipulator 1-5 includes a bottom plate 1-503 fixedly connected to the one of the top plates 1-502 in vertical direction and slidably connected with the frame body 1-1 in lateral direction, up and down driving cylinders 1-504 (double-stroke cylinder) with a cylinder body fixedly connected to the bottom plates 1-503 and movable ends oriented downwards, mounting plates 1-505 connected with the movable ends of the up and down driving cylinders 1-504, up and down moving splints 1-506 having one end fixedly connected to the mounting plates 1-505 and being slidably connected with the bottom plates 1-503 in vertical direction. The backward and forward sliding of the top plates 1-502 brings the bottom plates 1-503 to slide backwards and forwards on the frame body 1-1 so that the output side manipulator 1-6 and the inlet side manipulator 1-5 move backwards and forwards synchronously. The operation of the up and down driving cylinders 1-504 brings the mounting plates 1-505 and the up and down moving splints 1-506 to vertically move on the frame body 1-1 so as to move the manipulators upwards and downwards. The gripping parts include clamping cylinders 1-507 fixed on the bottom face of the mounting plates 1-505, two pneumatic claws 1-508 connected with the two movable ends of each of the clamping cylinders 1-507, insulation members 1-509 connected to the outer side of the pneumatic claws 1-508, the outer sides of the insulation members 1-509 threadingly connect connecting plates 1-510 connected with movable ends of the clamping cylinders 1-507, each of the opposite sides of the two pneumatic claws 1-508 is provided with a semi-circular slot to form a holding hole 1-511 matching with the core-penetrating copper bar 1-2. The operation of the clamping cylinders 1-507 brings the connecting plates 1-510, the insulation members 1-509 to operate so as to control the degree of opening or shutting of the two pneumatic claws 1-508 to grip or release the core-penetrating copper bar 1-2.

For improving the examination efficiency and avoiding high temperature caused by excessive large current, the examining system includes the insulation test devices 5 and the error examining modules 6, each of the insulation test devices 5 and the error examining modules 6 includes two core-penetrating mechanisms, each of the core-penetrating mechanism includes an inlet side manipulator 1-5, an output manipulator 1-6 and a core-penetrating copper bar 1-2. The two core-penetrating mechanisms are connected to the power source by means of a relay. Through switching by the relay, the two core-penetrating copper bars 1-2 let through large current in sequence so as to assure that only one core-penetrating copper bar 1-2 lets through the large current at the same time while the other one is on standby.

Each pallet 1-7 may load two bus-type current transformers 1-3, and three pallets 1-7 form a set. Brought along by the conveying line 1-4, the six bus-type current transformers 1-3 are penetrated by a core-penetrating copper bar 1-2 or released from the core-penetrating copper bar 1-2 in sequence, so that the six bus-type current transformers 1-3 can be examined at the same time. Thus twelve bus-type current transformers can be examined and tested in one insulation device 5 or one error examining module 6 in sequence.

The core-penetrating copper bar 1-2 for transformers according to embodiments of the present application keeps rest in a center position, and the transformers are brought along by the conveying line 1-4 to be penetrated. Thus the insulation test devices 5 and the error examining modules 6 have compact and simple structures and the core-penetrating can be performed with high success rate.

Since the heights of center holes and secondary windings of different transformers have big differences from each other. For adapting for the primary core-penetrating and secondary connecting for all types of transformers, the primary core-penetrating mechanism and secondary connecting mechanism may adopt double-stroke cylinder, and the moving stroke can be adjusted according to different sizes of transformers.

Figure 4:
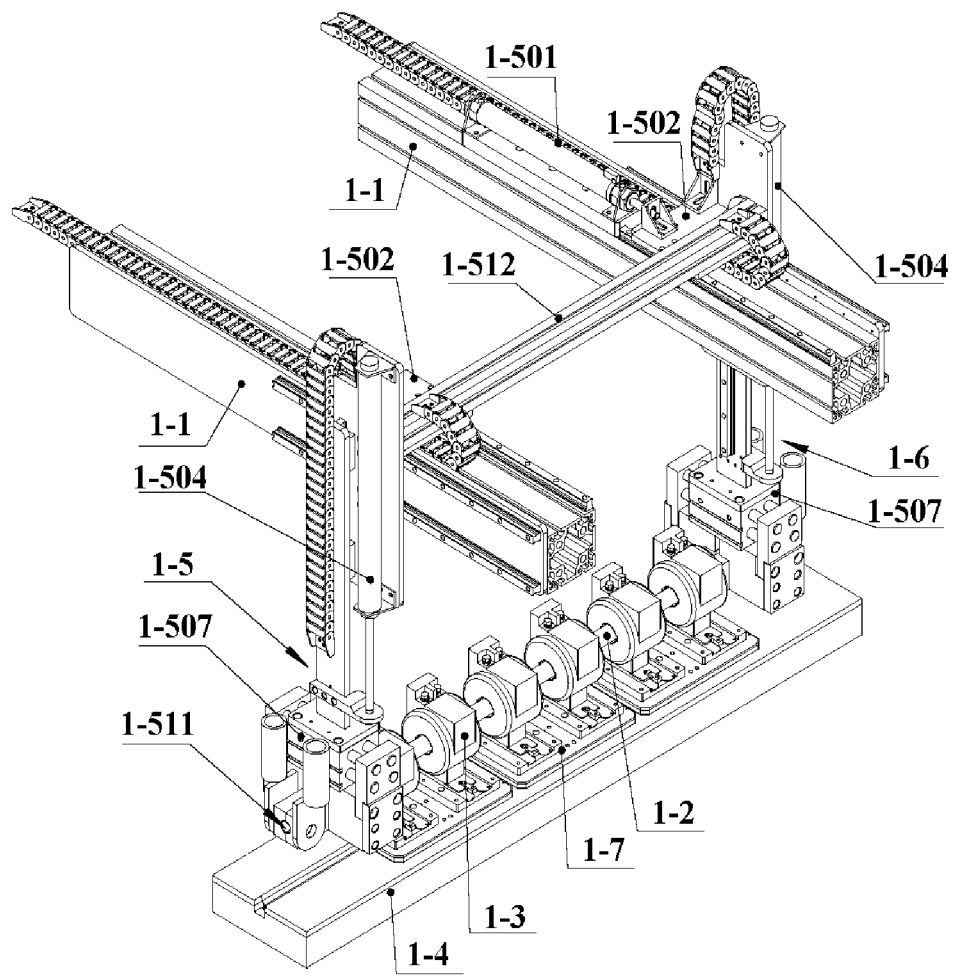
FIG. 4 is a schematic perspective view showing the structure of the primary core-penetrating mechanism according to embodiments of the present application.
Figure 5:
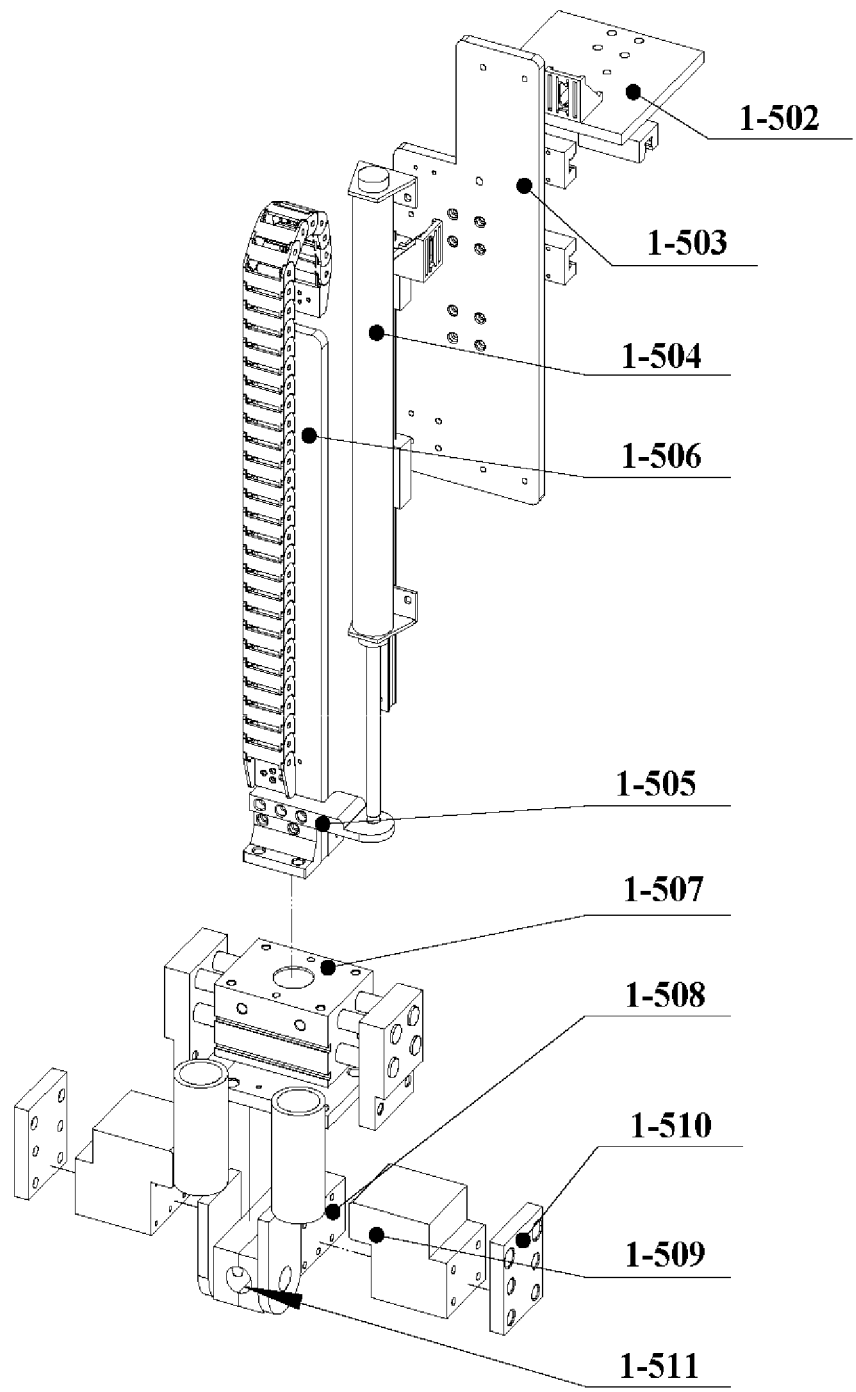
FIG. 5 is an exploded view of a manipulator of the primary core-penetrating mechanism according to embodiments of the present application.

Referring to FIG. 4, since for all types of transformers to be examined, diameters of the holes for penetration and the heights of the centers are different, if the core-penetrating copper bar 1-2 keeps the same height all along, it will has difficulty in prime penetrating for all types of transformers. The double-stroke cylinder 1-504 is adopted so that the fixtures and the primary copper bar may be brought to displace in the direction perpendicular to the examination conveying line body, and achieves positions of two heights of the primary copper bar, thereby fulfilling the requirement of primary core-penetrating for all types of transformers.

When on standby, the manipulator and the core-penetrating copper bar rest on the other side of the examination conveying line 4, and are arranged symmetry to the fixtures of the multi-turn-type current transformers. When the bus-type transformers are conveyed to the examining station, the manipulator translates to the center of the examination conveying line 4 along with the core-penetrating copper bar, waits and performs the operation of primary core-penetrating and primary connecting.

The secondary wire connecting mechanism includes an up and down driving assembly connected to the frame body and movable upwards and downwards, the lower end of the up and down driving assembly for secondary wire connecting is provided with multiple vertical conductive bars for connecting with secondary terminals of transformers.

Figure 16:
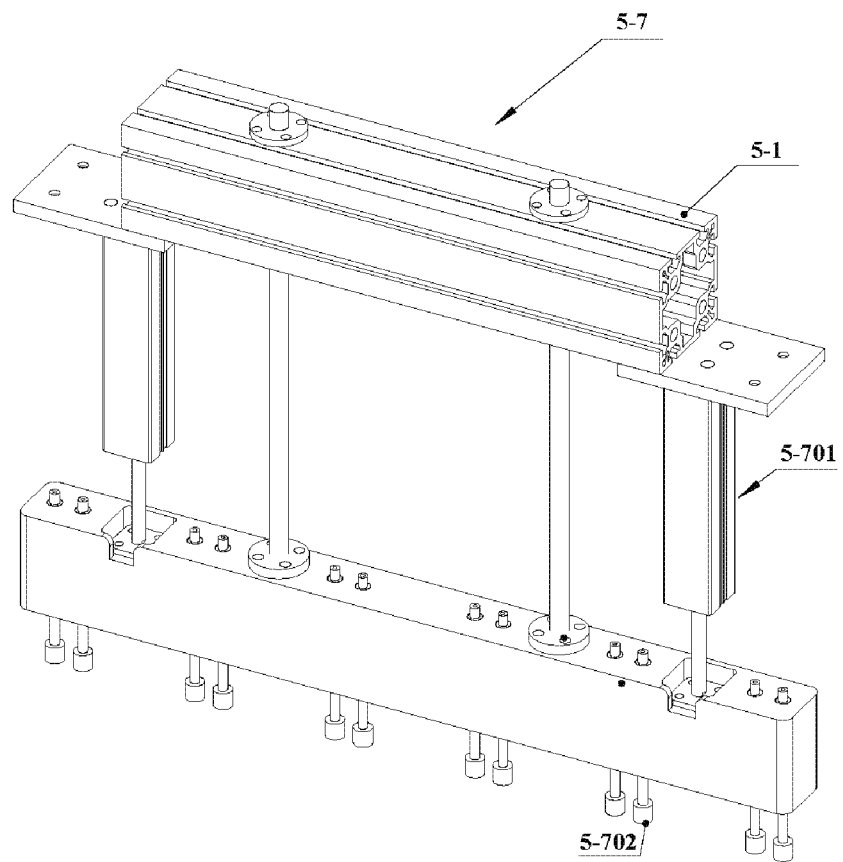
FIG. 16 is a schematic structural view of a secondary wire connecting mechanism according to embodiments of the present application.

As shown in FIG. 16, the secondary wire connecting mechanism 5-7 includes an up and down driving assembly for secondary wire connecting 5-701 connected with the frame body 5-1 and movable upwards and downwards, the lower end of the up and down driving assembly for secondary wire connecting 5-701 is provided with multiple vertical conductive bars 5-702 for connecting with the secondary terminals of transformers.

Now illustration will be made taking the secondary wire connecting mechanism for error testing for an example. The structure of the secondary wire connecting mechanism for error testing is substantially the same as that of the secondary wire connecting mechanism of the insulation test device 5, the differences lie in that the insulation test device 5 has two rows of conducting rods which are adapted to communicate the peak voltage meter and the output of the voltage boosting source, so as to perform the inter-turn insulation test, insulation resistance test, and power frequency withstand voltage test, which will not be described in detail herein.

Figure 8:
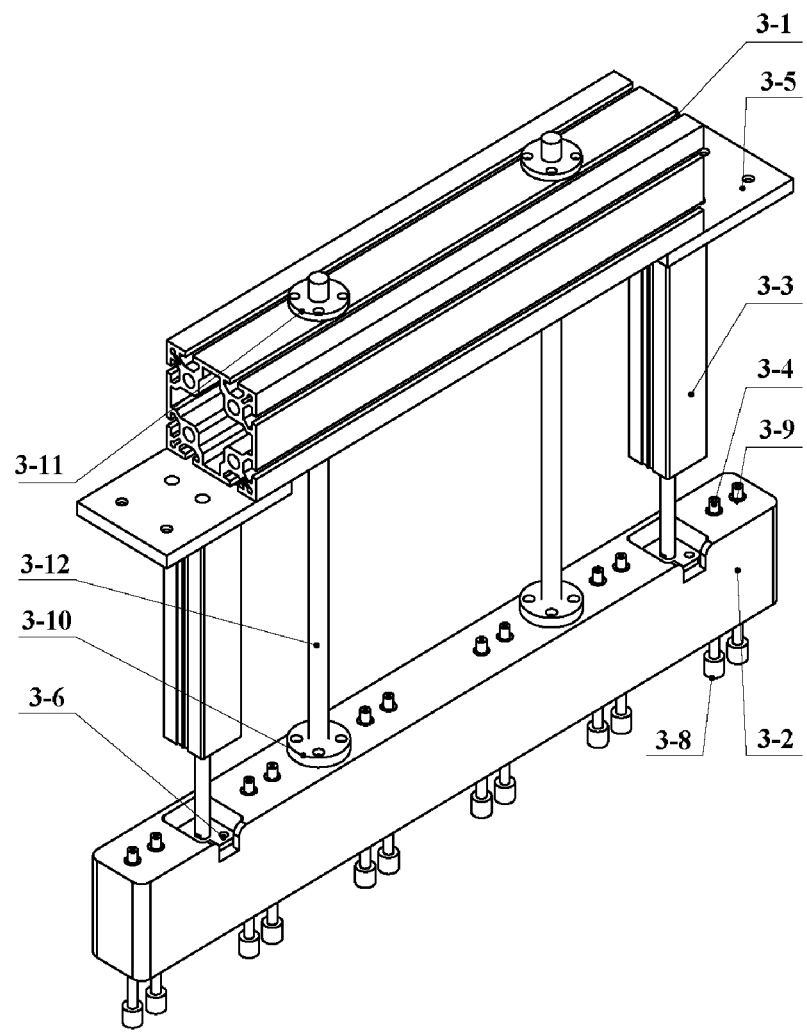
FIG. 8 is a schematic structural view of a secondary wire connecting mechanism for error testing according to embodiments of the present application.
Figure 9:
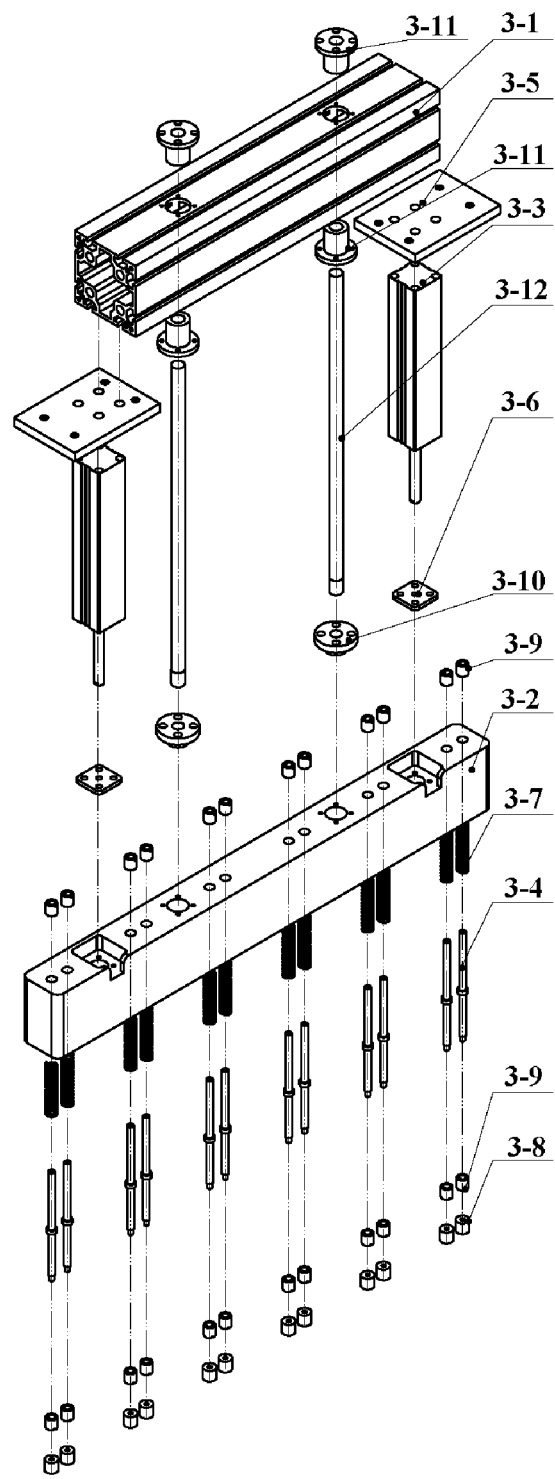
FIG. 9 is an exploded view of the secondary wire connecting mechanism for error testing according to embodiments of the present application.
Figure 10:
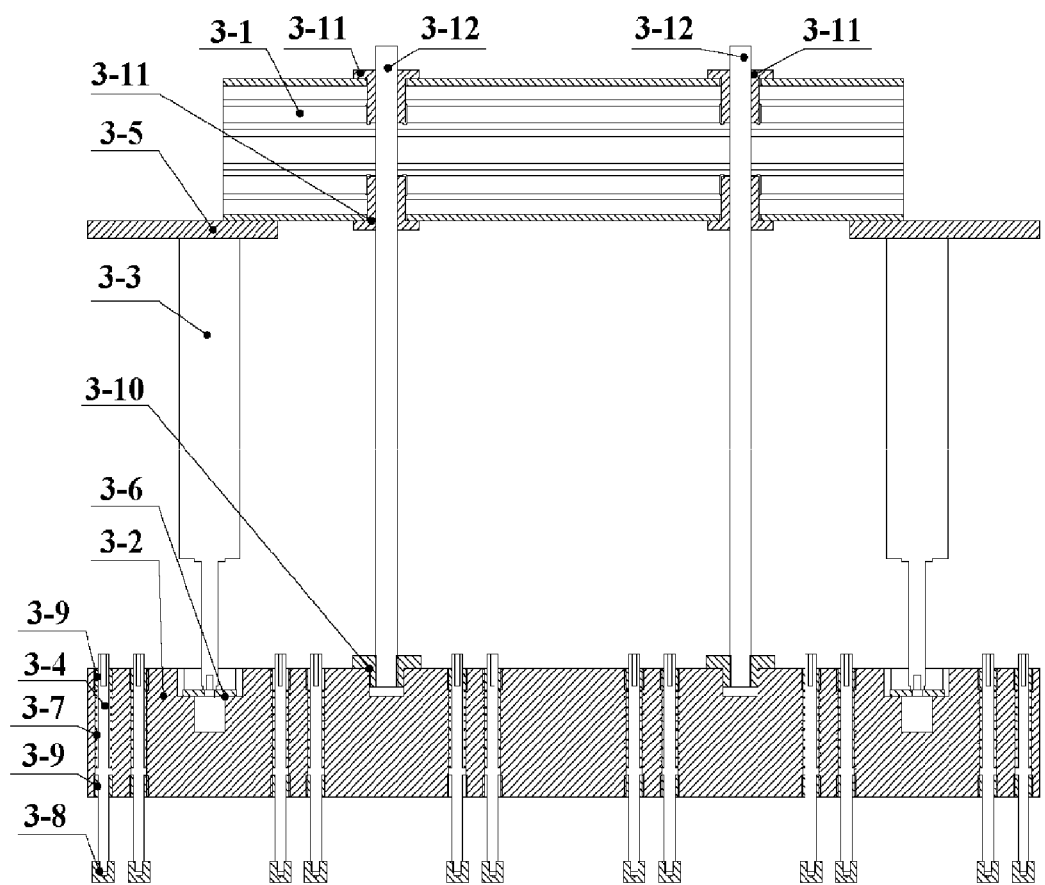
FIG. 10 is a sectional view of the secondary wire connecting mechanism for error testing according to embodiments of the present application.

As shown in FIGS. 8 to 10, the secondary wire connecting mechanism for error testing according to the present application includes a frame body 3-1, a strip-shaped insulation member 3-2 arranged under the frame body 3-1, a cylinder 3-3 (double-stroke cylinder) arranged between the frame body 3-1 and the insulation member 3-2 for driving the insulation member 3-2 to move upwards and downwards, a guiding rod 3-12 connected to the frame body 3-1 and the insulation member 3-2, and multiple testing probes 3-4 arranged side by side on the insulation member 3-2 for being connected with the secondary ends of transformers, with the upper ends of the testing probes 3-4 connected to leads.

Two cylinders 3-3 are provided between the frame body 3-1 and the insulation member 3-2, with the two cylinders 3-3 being respectively arranged at both ends of the insulation member 3-2. The cylinder body of the cylinder 3-3 is mounted vertically downwards on the lower end face of the frame body 3-1 via a connecting plate 3-5. The movable end of the cylinder 3-3 is fixed on the insulation member 3-2 via a bottom plate 3-6 for providing driving force to the insulation member 3-2 for moving upwards and downwards.

The lower end face of the frame body 3-1 is provided with two nut-mounting grooves, with each of the grooves being embedded with a nut member. The connecting plate 3-5 is locked to the nut members embedded into the nut-mounting grooves by bolts. The cylinder body of the cylinder 3-3 is fixed on the frame body 3-1 with the cylinder body of the cylinder 3-3 being fixed on the lower end face of the connecting plate 3-5 via connecting members.

The testing probes 3-4 each has a spring 3-7 sleeved thereon, the insulation member 3-2 is provided with multiple testing probe inserting holes, the middle portions of the testing probes 3-4 are provided with shoulders for abutting against springs 3-7. Each testing probe 3-4, with the spring 3-7 sleeved thereon, is inserted into one of the testing probe inserting holes. The lower ends of the testing probes 3-4 are provided with external threads for connecting copper heads 3-8 which abut against the secondary ends of transformers. One end of each spring 3-7 abut against the shoulders of the testing probes 3-4, with the other end of the spring 3-7 abutting against the insulation member 3-2 so that the insulation member 3-2 are rendered to move downwards and the testing probes 3-4 can reliably connect the secondary ends of transformers. Each of the upper and lower ends of the testing probes is provided with internal thread for connecting with the external threads of two shaft sleeves 3-9 respectively. The shaft sleeves 3-9 located at upper ends of the testing probes 3-4 have springs 3-7 sleeved on the testing probes 3-4 arranged between the lower end faces of the shaft sleeves 3-9 and the shoulders of the testing probes 3-4. When on standby, the shoulders of the testing probes 3-4 abut against the shaft sleeves 3-9 at lower ends of the testing probe inserting holes under the action of the elasticity of the springs 3-7. Guiding rods 3-12 are provided with twelve testing probes inserting holes side by side for inserting twelve testing probes 3-4. The number of the guiding rods 3-12 for connecting the frame body 3-1 and the insulation member 3-2 is two. The lower ends of the guiding rods 3-12 are fixed on the insulation member 3-2 via flanges 3-10. The frame body 3-1 is provided with guiding-rod holes for passing-through the guiding rods 3-12. Each of the guiding-rod holes is provided with two sliding bearings 3-11 fixedly connected to the lower and upper end faces of the insulation member 3-2 respectively via bolts. Leads connected with the upper ends of the testing probes 3-4 are connected to a check gauge for transformers so as to detect the secondary winding circuits of transformers when being tested for error. The lower ends of the copper heads 3-8 are provided with chamfering edges for avoiding interference with the insulation members in the middle of the secondary windings of transformers during connecting. Testing probes 3-4 together with leads connected to the upper ends of testing probes 3-4 form wire-connections for secondary winding circuits required by error testing of transformers. The sum of the contact resistances when testing probes are pressed to connect and the resistances of the leads connected to the upper ends of testing probes is the secondary circuit impedance for examining transformers which meets the requirement of the measuring and examining regulations.

The secondary connecting mechanism may perform the concurrent connection of the secondary windings of six transformers. During error testing, two testing probes 3-4 for the secondary winding of the same transformer are shorted by a relay, and thus are in a short circuit state. Through switching relays in sequence, the six transformers are connected to the check gauge for transformers in sequence, and are tested according to testing regulations for transformers.

Referring to FIG. 8, since the secondary terminals of the various types of transformers to be examined have two kinds of height, and the double-stroke cylinder 3-3 may be adopted so as to allow the testing probe to have two optional strokes when moving downwards, and a reasonable stroke may be chosen according to different types and measures of transformers for connecting reliably the secondary winding terminals of all types of transformers.

The positions of the secondary terminals of a bus-type transformer are the same as those of a multi-turn type transformer, hence the same set of mechanism for connecting the secondary winding is adopted in the present application. The secondary winding connecting mechanism in each of the insulation test devices 5 has two rows of terminals. One row of terminals are adapted to perform the insulation resistance measure and the power frequency withstand voltage test, through switching the relays, the secondary terminals may output voltage of DC 500V and AC 3000V, and through measuring the leakage current at the ground end, the insulation resistance of a transformer being examined can be measured. The other row of terminals are connected to measuring device, and when the primary winding allows through rated current of a transformer being examined, the peak voltage generated by the secondary open circuit is measured and monitored from the secondary terminals for determining the inter-turn insulation strength of the transformer. The measure and monitor devices measure and monitor the current raising capacity of the primary winding, peak voltage of the secondary winding, the leakage current of the ground end or the like of a transformer. Each of the error examining devices arranged beside the examination conveying line 4 and following insulation test devices 5 respectively is mainly composed of current transformers with current booster, primary leads, a primary winding connecting mechanism, a secondary winding connecting mechanism, a programmed control power source, a check gauge for transformers, a load box or the like. The insulation test devices 5 mainly perform tests such as basic error measurements and the magnetic saturation margins for low voltage current transformers. The current transformers with current booster, the primary leads, the primary winding connecting mechanism, the programmed control power source in the error examining devices 6 are the same as those in the insulation test devices 5, where the secondary winding connecting mechanism has only one row of terminals connected to the check gauge for transformers, for measuring the output current of the secondary windings of transformers. The check gauge for transformers and the load box are all of programmed control and can perform fully automatic examination.

Figure 11:
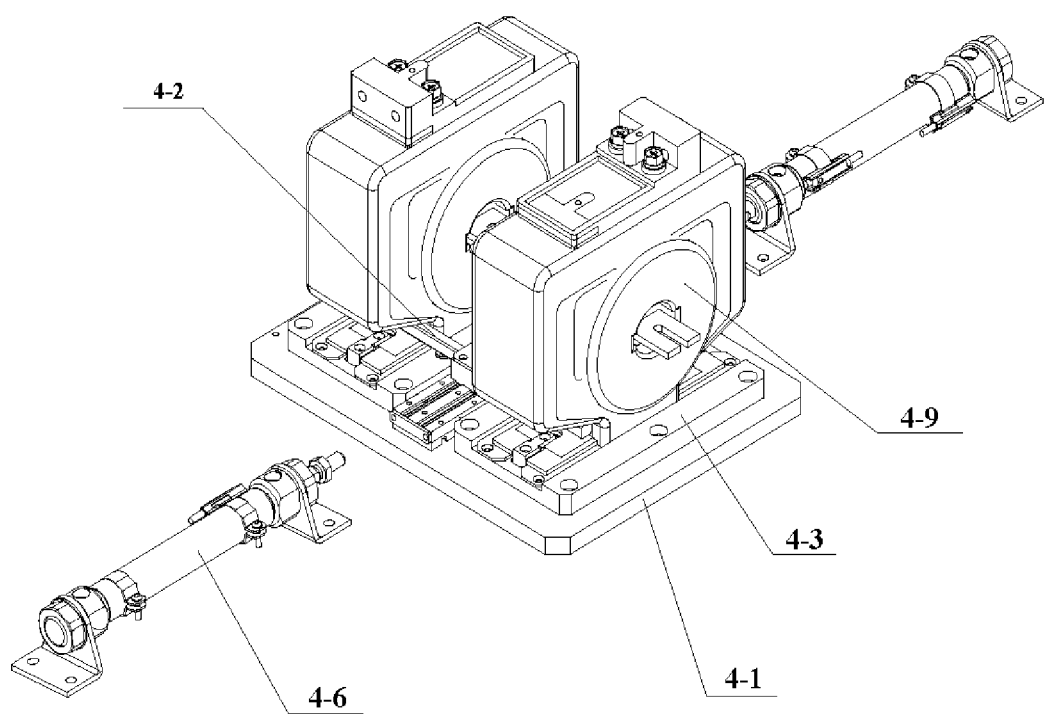
FIG. 11 is a schematic structural view of a pallet for on-line examination of transformers when being used according to embodiments of the present application.
Figure 12:
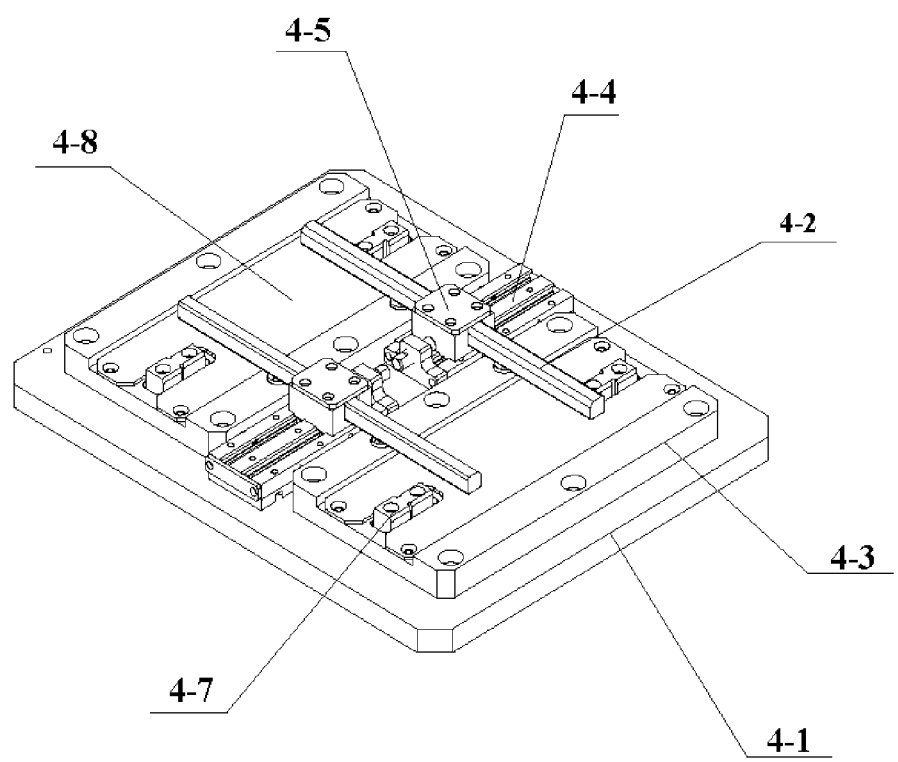
FIG. 12 is a schematic structural view of the pallet for on-line examination of transformers according to embodiments of the present application.
Figure 13:
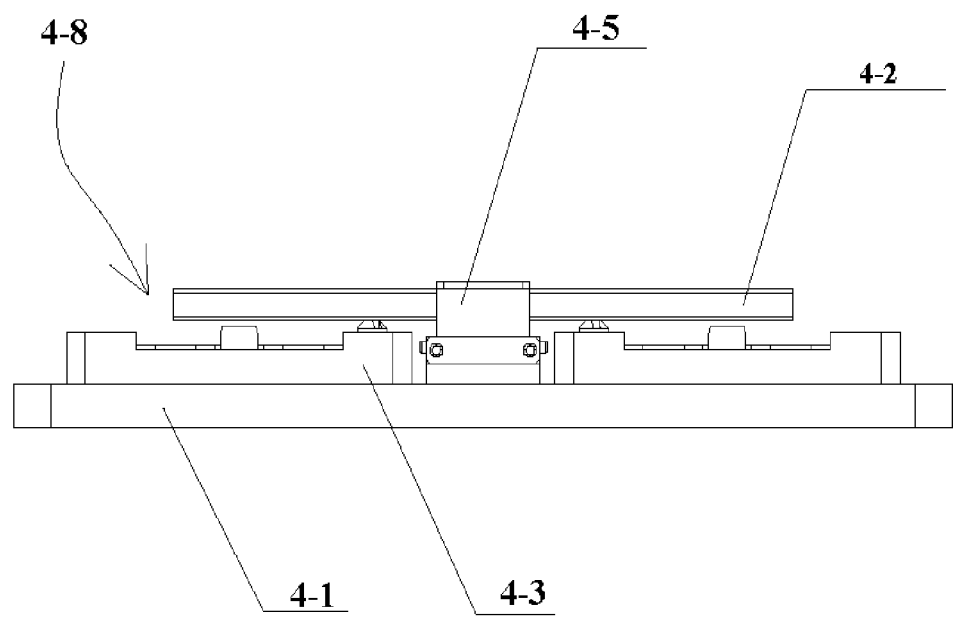
FIG. 13 is a front view of the pallet for on-line examination of transformers according to embodiments of the present application.

As shown in FIGS. 11 to 13, the pallet for on-line examination of transformers according to embodiments of the present application (i.e. the pallets 10 in FIG. 1) includes a base plate 4-1, two stop levers 4-2 movable backwards and forwards mounted on the base plate 4-1, insulation backing plates 4-3 mounted on the base plate 4-1 under the stop levers. Two guide rails 4-4 are provided on the base plate 4-1 along the center line of the base plate 4-1. Each of the guide rails 4-4 is slidably connected with a sliding block 4-5. A stop lever 4-2 is mounted on each of the sliding bocks 4-5. An insulation backing plate 4-3 is mounted on each side of the guide rail 4-4. The stop levers 4-2 and the insulation backing plates 4-3 are in clearance fitting. The sliding blocks 4-5 are driven by cylinders 4-6. Each of the front and back edges of the insulation backing plates 4-3 is provided with a positioning hole. The base plate 4-1 is provided with positioning pins 4-7 matching with the positioning holes. The insulation backing plates 4-3 are provided with grooves 4-8 along the backward and forward directions in the middle of the insulation backing plates 4-3.

Operating process: when the automatic production line body charges transformers 4-9, cylinders 4-6 make stop levers 4-2 return, and after transformers 4-9 in a transformer box are picked out and placed on the insulation backing plates 4-3 by a material charging manipulator, with cylinders 4-6 stretching out, transformers 4-9 are stuck in floating by stop levers 4-2, and then enter the automatic production line body to be measured and examined.

The examination management system includes a task managing functional module, a conveyance control functional module, an examination control functional module, a data process and analysis functional module.

The task management functional module is adapted to obtain a working task from a production scheduling platform, and apply for sending materials out with the storage system, decompose the task for different examining units and stations according to the production task.

The conveyance control functional module is adapted to trigger material charging and material discharging robots to charge and discharge materials automatically, control the conveying line to distribute the transformers to be examined to corresponding examining stations, and charge and discharge materials in sequence for multiple sets of examining devices and multiple examining units.

The examining control functional module is adapted to automatically perform the connecting of the primary windings and the secondary windings required for examinations of transformers, control the current booster and voltage booster and measure to fulfill the examinations, and store error data.

The data process and analysis functional module is adapted to determine whether a transformer is examined to be qualified, and perform analysis and statistics on the finishing rate and failure rate of the examining tasks for transformers.

Figure 2:
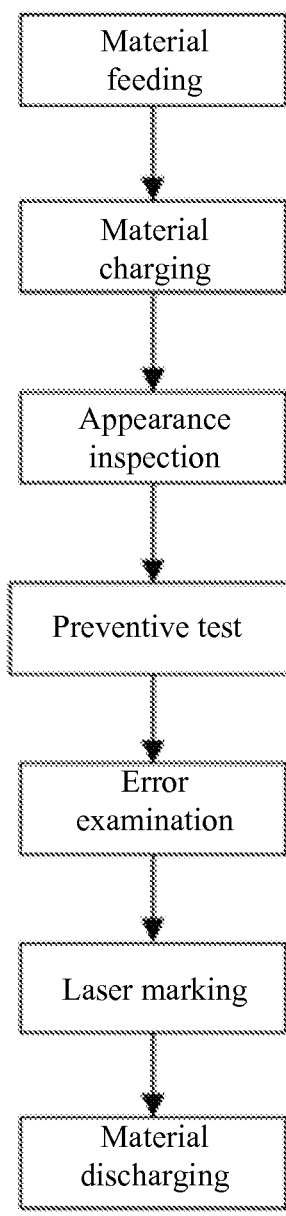
FIG. 2 is a flowchart showing the operations of the system for examining transformers full-automatically according to embodiments of the present application.
Figure 3:
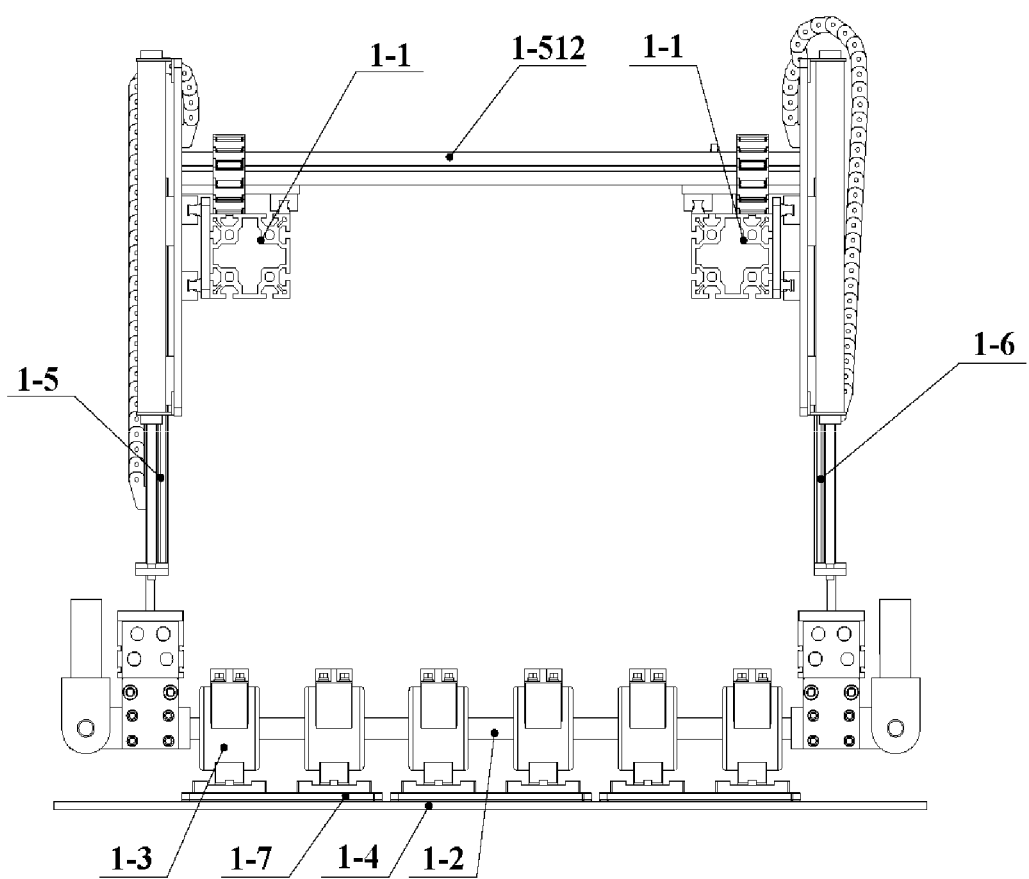
FIG. 3 is a schematic planar view showing the structure of a primary core-penetrating mechanism according to embodiments of the present application.

Referring to FIG. 2, FIG. 2 is a flow chart showing the operations of the system for examining transformers full-automatically according to embodiments of the present application.

The examining method corresponding to the system for examining transformers full-automatically according to embodiments of the present application includes steps as follows:

1) Material Feeding Step

Instrument transformers are conveyed from exit of the storage system to material charging station by material conveying line 2.

2) Material Charging Step

Instrument transformers on the material conveying line 2 are grasped and placed onto the pallets 10 located on the examination conveying line 4 by a robot, the pallets 10 are bound with bar code information of corresponding transformers, and information of transformers is recorded.

3) Appearance Inspection Step

The pallets 10 are brought along by the examination conveying line 4 and enter into an appearance inspection station, the camera takes photos of transformers, and through contrasting the photos taken with the corresponding photos stored, the appearance inspection device analyzes whether the content of the name plate of a transformer to be examined is complete and the body of the transformer to be examined is in good condition, and records.

4) Insulation Test (Preventive Test) Step

The pallets 10 arrive at insulation test stations along with the examination conveying line 4, certain numbers of pallets 10 are brought along by the examination conveying line 4 and enter into the corresponding insulation test stations, the insulation test devices 5 at the insulation test stations connect primary windings and secondary windings of transformers, programmed control power source outputs voltages of 380V or 220V to current booster and voltage booster, so that the current booster generates low voltage large current and the voltage booster generates DC and AC voltages according to different tests to perform the inter-turn insulation test, the insulation resistance test and the power frequency withstand voltage test in sequence for low voltage current transformers.

5) Error Examining Step

When the insulation test finishes, the transformers being examined flow into the error examining station along with the examination conveying line 4, the error examining devices at the error examining stations connect the primary windings and the secondary windings of transformers, the programmed control power source outputs voltages of 380V or 220V to the current booster, the current booster generates low voltage large current which flows through the primary windings of transformers to be measured in series connection via primary leads connected to the output end of the current booster. The output currents of the secondary windings of transformers are measured by a check gauge for transformers connected to the secondary winding connecting mechanism, the error test and the magnetic saturation margin test are performed, full-automatic examination is realized, and unqualified products are recorded.

6) Laser Marking Step

After the error examining finishes, the pallets 10 enter into a laser marking station along with the examination conveying line 4. The laser marking machine will etch a section of codes on the body of the transformer examined to be qualified. The transformers examined to be unqualified flow into the material discharging stations automatically and wait for abnormal handling without being marked by laser.

The codes are adapted to indicate the information of being examined to be qualified, an examination date, and the personnel performing the examination.

7) Material Discharging Step

The qualified transformers on the pallets 10 on the examination conveying line 4 are grasped and placed in the boxes located on the material conveying line 2 by a robot, and after the transformers are boxed, the boxes are conveyed to the storage system along with the material conveying line 2.

Each of the insulation test devices 5 and the error examining devices 6 is divided into a first examining unit and a second examining unit. A batch of twelve transformers is divided into two equal groups which enter into the first examining unit and the second examining unit in sequence. When the first examining unit of the insulation test device 5 electrifies and tests six transformers, the second examining unit of the insulation test unit 5 finishes wires connecting of the first windings and the second windings, and waits for electrifying and testing. After the first examining unit of the insulation test device 5 finishes electrifying and testing the six transformers, the second examining unit of the insulation test device 5 begins the electrifying and testing. Subsequently, six transformers in the first examining unit of the insulation test device 5 flow into the first examining unit of one of the error examining devices 6, and are electrified and tested after being wired. After the second examining unit of the insulation test device 5 finishes electrifying and testing the six transformers, six transformers having flowed into the second examining unit of the error examining device 6 are electrified and tested.

In the present technical solution, different primary wire connecting mechanisms are designed for bus-type current transformers and multi-turn-type current transformers respectively so as to meet different wire connecting requirements, while same set of secondary end wire connecting mechanism is used for the two different types of transformers since the same measurements of the secondary ends of the two types of transformers. When examining the secondary inter-turn insulation, since allowing through large current for a long time is required, the primary wire connecting mechanism will generate huge amount of heat. The significant temperature rise will decrease the service life of the large current lead and the mechanism, hence when designing the device, a batch of twelve transformers are divided into a left group and a right group with each of the groups having 6 stations so as to reduce the electrifying period for each mechanism and enable each mechanism to have more time for dissipating heat.

One, steps of performing insulation test and error examination on bus-type current transformers by the present device are as follows:

1) The software of examination management system obtains a working task from the production scheduling platform, and decomposes the task for different stations of different examining devices. The examining control software of the automatic examining devices for transformers obtains the task, and makes related preparations.

2) When the examining devices ensure that the objects to be examined in the present batch are bus-type transformers, the primary wire connecting mechanism for bus-type current transformers of the first examining unit of the insulation test device pushes to the middle position of the conveying line, so as to keep the height of the core-penetrating copper bar in vertical direction and the position of the core-penetrating copper bar in lateral direction the same as the position of the center hole of transformers on conveying line.

3) When transformers to be examined are stopped at the sorting station on the conveying line, this batch of transformers is ascertained to enter into the automatic examining device should be entered through an identity identification procedure.

4) When the automatic examining device obtains trigger signal sent from the conveying management software, the pneumatic claw 5-504 at lower end of the inlet side manipulator 5-502 of the insulation test unit releases the core-penetrating copper bar, later, the inlet side manipulator 5-502 rises and gets out of the inflow passage of transformers, at this point, the core-penetrating copper bar is gripped by only one side with the other side in suspension.

5) After transformers to be examined being penetrated by the core-penetrating copper bar from the left side of the core-penetrating copper bar are conveyed to examining stations, a positioning feedback signal is simultaneously transmitted to a examining control software by a stop mechanism in the station, after receiving the above signal, the examining control software believes that transformers have been in the examining stations, and controls the output side manipulator to come down, and the pneumatic claw 5-504 grips the core-penetrating copper bar.

6) The up and down driving assembly for secondary wire connecting 5-701 of the secondary wire connecting mechanism 5-7 hanging over the first examining unit comes down so as to allow the conductive rod 5-702 to contact the secondary end of transformers.

7) After finishing wire connecting for the primary and secondary windings of transformers, the examining device pre-boosts the current of transformers to detect the open circuit voltage of the secondary end of each transformer, for examining whether the wire connecting of the primary and secondary windings of transformers is reliable.

8) After wire connecting is finished, the examining instruments in the insulation test devices perform the insulation resistance test, the power frequency withstand voltage test and the secondary inter-turn insulation test on transformers according to examination specifications, and upload the test results to the examining control software.

9) At the same time when the first examining unit of the insulation test device operates, the examining control software controls the second examining unit to operate in a same process as that of the first group bus-type current transformers entering into the first examining unit, thus finishing automatic wire connecting and automatic testing for insulation tests of the second group transformers to be examined.

10) After finishing the tests of the first examining unit, the pneumatic claw 5-504 at lower end of the inlet side manipulator releases the core-penetrating copper bar, the output side manipulator moves upwards, at this point, again only one side of the core-penetrating copper bar is gripped, and the other side is in suspension, and transformers flow rightwards out of the station.

11) When the transformers on the stations all flow out, an infrared sensor and counter on the conveying line will feedback information to confirm that transformers on the conveying line have all flowed out. The output side manipulator comes down, so that the pneumatic claw at the lower end of the output side manipulator grips the core-penetrating copper bar, subsequently, the whole primary wire connecting mechanism for bus-type current transformers is moved away from the conveying belt and placed in a safe position by the back and forth driving assembly for bus-type current transformers.

12) After being examined, transformers in the second examining unit flow out in a process the same as that of the first group transformers.

13) After having an insulation test, the first group of transformers flows directly into the first examining unit of the error examining device. And after having an insulation test, the second group of transformers flows into the second examining unit of the error examining device. The processes of flowing in and out for the two groups of transformers are the same as those in the insulation test devices.

Two, the steps of performing insulation test and error examination on the multi-turn-type current transformers by the present device are as follows:

According to the present device, the method for examining multi-turn-type current transformers is substantially the same as that for examining bus-type current transformers. The difference lies in that, when multi-turn-type current transformers enter, the primary wire connecting mechanism for multi-turn-type current transformers of the first or the second examining unit operates, while the primary wire connecting mechanism for bus-type current transformers keeps rest, the back and forth driving assembly for multi-turn-type current transformers moves towards the conveying belt, subsequently, the primary ends of transformers are held by the connecting assembly 5-602, so that primary sides of multiple transformers are connected in series. After the examination finishes, the connecting assembly 5-602 releases the primary ends of transformers, and the back and forth driving assembly goes away from the conveying belt and exits the test stations.

The above description is only preferred embodiments of the present application, the protection scope of the present invention is not limited to those embodiments, any variations and modifications which can be envisioned without efforts by those ordinary skilled in the art within the technical scope disclosed in the present application should be covered in the protection scope of the present application. Hence, the protection scope of the present application should only be limited by the claims.

The invention claimed is:

1. A system for examining transformers full-automatically, comprising: a material conveying line, a material charging device, an examination conveying line, an appearance inspection device, an insulation test device, an error examining device, a laser marking device, a material discharging device, and an examination management system; wherein the insulation test device, the error examining device, and the laser marking device are sequentially arranged along a direction of advance of the examination conveying line;

the material conveying line is adapted to deliver turnover boxes loaded with transformers to be examined from a storage system to a material charging station, and deliver turnover boxes loaded with transformers having been examined located at a material discharging station back to the storage system;

the material charging device, located beside the material charging station of the material conveying line, is adapted to move transformers located at the material charging station on the material conveying line to the examination conveying line;

the examination conveying line is adapted to move transformers to stations corresponding to respective devices;

the insulation test device is adapted to detect insulation resistances, test power frequency withstand voltages and test inter-turn insulations of transformers;

the error examining device is adapted to detect basic errors and magnetic saturation margins of transformers;

the laser marking device is adapted to imprint identification information on qualified transformers;

the material discharging device, located beside the material discharging station on the material conveying line, is adapted to transfer transformers having been examined from the examination conveying line to the material conveying line; and the examination management system is adapted to control coordinate operation of respective devices, the material conveying line and the examination conveying line and to sort transformers accurately according to feedback information from the insulation test device and the error examining device.

2. The system for examining transformers full-automatically according to claim 1, further comprising an appearance inspection device located ahead of the insulation test device, and adapted to take photos of the appearance of each transformer and checking.

3. The system for examining transformers full-automatically according to claim 2, wherein the material conveying line comprises a frame body, a driving motor arranged on the frame body for driving a belt to move forward, a belt connected with a rotating shaft of the driving motor, and/or a stop mechanism arranged on the frame body for stopping transformers on the belt accurately, and/or a counter arranged on the frame body for counting transformers, and/or a bar code scanner arranged on the frame body for entering information of transformers and a sorting mechanism for sorting transformers; an input end and an output end of the material conveying line are adapted to connect an entrance and an exit of the storage system respectively.

4. The system for examining transformers full-automatically according to claim 3, wherein the material charging device comprises a material charging robot for placing transformers to be examined from the material conveying line to the pallets on the examination conveying line precisely, the material charging robot is provided with a material charging manipulator, a controller for controlling the operation of the material charging manipulator, and a material charging fixture connected with an lower end of the manipulator; the material discharging device comprises a material discharging robot for placing transformers having been examined from the pallets on the examination conveying line to the material conveying line, the material discharging robot is provided with a material discharging manipulator, a controller for controlling the operation of the material discharging manipulator, and a material discharging fixture connected with a lower end of the material discharging manipulator.

5. The system for examining transformers full-automatically according to claim 4, wherein each of the material charging robot and the material discharging robot is provided with a positioning platform for positioning transformers precisely, transformers are grasped from the material conveying line and are placed on the positioning platform of the material charging robot by the material charging manipulator for being positioned, and after having been positioned, the transformers are grasped again and placed onto the pallets located on the examination conveying line by the material charging manipulator.

6. The system for examining transformers full-automatically according to claim 5, wherein each of the insulation test device and the error examining device comprises a second examining unit and a first examining unit which are sequentially arranged on the frame body beside the examining conveying line along the direction of advance of the examination conveying line;

connections between a power source and primary large current conductors of the first examining unit and the second examining unit are switched by means of a relay;

each of the first examining unit and the second examining unit comprises a primary wire connecting mechanism for bus-type current transformers, a primary wire connecting mechanism for multi-turn-type current transformers and a secondary wire connecting mechanism; and both the primary wire connecting mechanism for bus-type current transformers and the primary wire connecting mechanism for multi-turn-type current transformers are capable of moving backwards and forwards, and are respectively arranged on both sides of examination conveying line when both the primary wire connecting mechanism for bus-type current transformers and the primary wire connecting mechanism for multi-turn-type current transformers are on standby.

7. The system for examining transformers full-automatically according to claim 6, wherein the primary wire connecting mechanism for bus-type current transformers comprises a back and forth driving assembly for bus-type current transformers, an inlet side manipulator and an output side manipulator, pneumatic claws, and a core-penetrating copper bar, the back and forth driving assembly for bus-type current transformers, is capable of moving backwards and forwards on the frame body;

the inlet side manipulator and the output side manipulator are connected with left and right ends of the back and forth driving assembly respectively and are capable of moving upwards and downwards;

the pneumatic claws are arranged at lower ends of the inlet side manipulator and the output side manipulator and can open and shut;

the core-penetrating copper bar, gripped by the pneumatic claws, is adapted to penetrate a plurality of bus-type current transformers;

outer sides of the pneumatic claws are provided with column-shaped copper heads for connecting with the large current conductor, the two pneumatic claws and the core-penetrating copper bar of the primary wire connecting mechanism for bus-type current transformers are capable of forming a closed circuit of bus-type;

the primary wire connecting mechanism for multi-turn-type current transformers comprises a back and forth driving assembly for multi-turn-type current transformers which is capable of moving backwards and forwards on the frame body, a plurality of connecting assemblies arranged side by side on the back and forth driving assembly for connecting in series primary sides of the corresponding multi-turn-type current transformers;

the connecting assembly comprises upper and lower conductive holding members capable of holding terminals on the primary side of multi-turn-type current transformers; and the secondary wire connecting mechanism comprises an up and down driving assembly for secondary wire connecting which is connected with the frame body and capable of moving upwards and downwards, the lower end of the up and down driving assembly for secondary wire connecting is provided with a plurality of vertical conductive bars for connecting the secondary end of transformers.

8. The system for examining transformers full-automatically according to claim 7, wherein the secondary wire connecting mechanism comprises a frame body, a strip-shaped insulation member arranged under the frame body, a cylinder arranged between the frame body and the insulation member for driving the insulation member to move upwards and downwards, a guiding rod connected to the frame body and the insulation member, and a plurality of testing probes arranged side by side on the insulation member for being connected with secondary ends of transformers; with upper ends of the testing probes connected to leads, lower end of the testing probes adapted to be connecting ends for being connected with wire connecting ends of secondary windings of transformers to be examined; and two cylinders are provided between the frame body and the insulation member, with the two cylinders being respectively arranged at both ends of the insulation member, the cylinder body of the cylinder is mounted vertically downwards on a lower end face of the frame body via a connecting plate, and a movable end of the cylinder is fixed on the insulation member via a bottom plate for providing driving force to the insulation member for moving upwards and downwards.

9. The system for examining transformers full-automatically according to claim 8, wherein each of the testing probes has a spring sleeved thereon, the insulation member is provided with a plurality of testing probe inserting holes matching with the testing probes, the middle portions of the testing probes are provided with shoulders for abutting against the springs, each testing probe, with the spring sleeved thereon, is inserted into one of the testing probe inserting holes, the lower ends of the testing probes are provided with external threads for connecting with copper heads which abut against the secondary ends of transformers; one end of each spring abut against the shoulder of the testing probe, with the other end of the spring abutting against the insulation member for providing a proper pressing force for the abutting of the testing probes against the secondary ends of transformers so as to achieve reliable connection between the testing probes and the secondary ends of transformers and meanwhile avoid damaging.

10. The system for examining transformers full-automatically according to claim 7, wherein the primary wire connecting mechanism for multi-turn-type current transformers comprises a connecting bracket, an upper insulation plate arranged above the connecting bracket, a lower insulation plate arranged below the connecting bracket, a cylinder connected to the lower insulation plate with a cylinder body fixed on the upper insulation plate and a movable rod passing through the connecting bracket, an upper conductive holding member and a lower conductive holding member which are located between the upper insulation plate and the lower insulation plate and are adapted to hold the primary terminal of multi-turn-type current transformers.

11. The system for examining transformers full-automatically according to claim 10, wherein the primary wire connecting mechanism for multi-turn-type current transformers further comprises a plurality of bracket guiding rods for guiding which are arranged by passing the connecting bracket with upper and lower ends of each of the guiding rods slidably connected with the upper and lower insulation plates respectively, the plurality of bracket guiding rods are parallel to the movable rod of the cylinder and are arranged respectively on both sides of the movable rod of the cylinder, and small compression springs sleeved on portions of the bracket guiding rods that between the upper insulation plate and the connecting bracket as well as between the lower insulation plate and the connecting bracket; the upper conductive holding member is slidably connected to the corresponding upper insulation plate by means of holding-member guiding rods with big compression springs sleeved on the guiding rods, the lower conductive holding member is slidably connected to the corresponding lower insulation plate by means of holding-member guiding rods with big compression springs sleeved on the guiding rods, with large current conductors for examination testing transformers being fixed on the top portion of each of the holding-member guiding rods.

12. The system for examining transformers full-automatically according to claim 10, wherein the connecting bracket is in a "Z" shape, and a fore part of the connecting bracket is connected with the upper and lower insulation plates, a rear end of connecting bracket is fixedly connected with the big splint movable backwards and forwards, a plurality of connecting brackets are fixed on one big splint so as to drag a plurality of wire connecting devices simultaneously, the upper and lower insulation plates of the wire connecting devices on the leftmost or rightmost side of the big splint are respectively provided with an upper conductive holding member and a lower conductive holding member opposite to the upper conductive holding member.

13. The system for examining transformers full-automatically according to claim 7, wherein the examination management system comprises:

a task management functional module, adapted to obtain a working task from a production scheduling platform, apply with the storage system for sending materials out, and decompose the task for different examining units and stations according to the production task;

a conveyance control functional module, adapted to trigger material charging and material discharging robots to charge and discharge materials automatically, control the conveying line to distribute the transformers to be examined to corresponding examining stations, and charge and discharge materials in sequence for a plurality sets of examining devices and a plurality of examining units;

an examining control functional module, adapted to automatically perform connecting of the primary winding and the secondary winding required for examinations of transformers, control a current booster and a voltage booster and a measure to fulfill the examinations, and store error data; and a data process and analysis functional module, adapted to determine whether a transformer is examined to be qualified, and perform analysis and statistics on finishing rate and failure rate of the examining tasks for transformers.

14. The system for examining transformers full-automatically according to claim 1, wherein the system is provided with a plurality of testing device sets arranged side by side, with each of the testing device set comprising one insulation test device and one error examining device which are arranged on a frame body beside the examination conveying line; and a head end and a tail end of the examination conveying line are connected, the examination conveying line is provided with pallets matching the examination conveying line which are adapted to load transformers to be examined.

15. The system for examining transformers full-automatically according to claim 3, wherein the pallet comprises a base plate, two stop levers movable backwards and forwards mounted on the base plate, insulation backing plates mounted on the base plate under the stop levers;

two guide rails are provided on the base plate along the same line of the base plate, each of the guide rails is slidably connected with a sliding block, a stop lever is mounted on each of the sliding bocks; and the sliding blocks are driven by cylinders.

16. A method for examining transformers full-automatically, wherein the method is applied in a system for examining transformers full-automatically, the system comprising: a material conveying line, a material charging device, an examination conveying line, an appearance inspection device, an insulation test device, an error examining device, a laser marking device, a material discharging device, and an examination management system; wherein the insulation test device, the error examining device, and the laser marking device are sequentially arranged along a direction of advance of the examination conveying line; the material conveying line is adapted to deliver turnover boxes loaded with transformers to be examined from a storage system to a material charging station, and deliver turnover boxes loaded with transformers having been examined located at a material discharging station back to the storage system; the material charging device, located beside the material charging station of the material conveying line, is adapted to move transformers located at the material charging station on the material conveying line to the examination conveying line; the examination conveying line is adapted to move transformers to stations corresponding to respective devices; the insulation test device is adapted to detect insulation resistances, test power frequency withstand voltages and test inter-turn insulations of transformers; the error examining device is adapted to detect basic errors and magnetic saturation margins of transformers; the laser marking device is adapted to imprint identification information on qualified transformers; the material discharging device, located beside the material discharging station on the material conveying line, is adapted to transfer transformers having been examined from the examination conveying line to the material conveying line; and the examination management system is adapted to control coordinate operation of respective devices, the material conveying line and the examination conveying line and to sort transformers accurately according to feedback information from the insulation test device and the error examining device, and the method comprises steps as follows:

1) material feeding step, wherein transformers to be examined are conveyed from an exit of the storage system to the material charging station by the material conveying line;

2) material charging step, wherein transformers on the material conveying line are grasped and placed onto the pallets located on the examination conveying line by a material charging robot, the pallets are bound with bar code information of transformers, and information of transformers is recorded;

3) appearance inspection step, wherein the pallets are brought along by the examination conveying line and enter into an appearance inspection station, a camera takes photos of the transformers, and through contrasting the photos taken to the corresponding photos stored, the appearance inspection device analyzes whether a content of a name plate of a transformer to be examined is complete and a body of the transformer to be examined is in good condition, and records;

4) insulation test step, wherein the pallets arrive at a corresponding insulation test station along with the examination conveying line, certain numbers of pallets are brought along by the examination conveying line and enter into the corresponding insulation test station, the insulation test device at the insulation test station connects primary windings and secondary windings of transformers, a programmed control power source outputs voltages of 380V or 220V to a current booster, the current booster generates a low voltage large current which flows through primary windings of transformers to be measured in series connection via primary leads connected to an output end of the current booster, and a value of the insulation resistances, a result of the power frequency withstand voltages and a result of the inter-turn insulations of low voltage current transformers are obtained through detecting at a ground end and a secondary end;

5) error examining step, wherein when the insulation test finishes, the transformers being examined flow into error examining stations along with the examination conveying line, the error examining device at the error examining stations connects the primary windings and the secondary windings of transformers, the programmed control power source outputs voltages of 380V or 220V to the current booster, the current booster generates a low-voltage large current which flows through primary windings of transformers to be measured in series connection via primary leads connected to the output end of the current booster, the output currents of secondary windings of transformers are measured by a check gauge for transformers connected to the secondary winding connecting mechanism, the error test and the magnetic saturation margin test are performed, full-automatic examination is realized, and unqualified products are recorded;

6) laser marking step, wherein after the error examining finishes, the pallets enter into a laser marking station along with the examination conveying line, the laser marking device etches a section of unique codes on the body of the transformer examined to be qualified; the transformers examined to be unqualified flow into the material discharging station automatically and wait for abnormal handling without being marked by laser; and 7) material discharging step, wherein the qualified transformers on the pallets on the examination conveying line are grasped and placed in the boxes located on the material conveying line by a material discharging robot, and after the transformers are boxed, the boxes are conveyed to the storage system along with the material conveying line.

* * * * *

UNITED STATES PATENT AND TRADEMARK OFFICE
CERTIFICATE OF CORRECTION

PATENT NO. : 9,562,916 B2
APPLICATION NO. : 13/980556
DATED : February 7, 2017
INVENTOR(S) : Wei Wang et al.

It is certified that error appears in the above-identified patent and that said Letters Patent is hereby corrected as shown below:

In the Claims

At Column 27, Claim 15, Line numbers 4-5 the claim should read as follows:

15. The system for examining transformers full-automatically according to claim 14, wherein the pallet comprises a Signed and Sealed this
Fourth Day of July, 2017

Joseph Matal
*Performing the Functions and Duties of the*
*Under Secretary of Commerce for Intellectual Property and*
*Director of the United States Patent and Trademark Office*